United States Patent
Wang et al.

(10) Patent No.: US 10,928,395 B2
(45) Date of Patent: Feb. 23, 2021

(54) PROTEIN AND AUTOANTIBODY BIOMARKERS FOR THE DIAGNOSIS AND TREATMENT OF LUNG CANCER

(71) Applicants: MagArray, Inc., Milpitas, CA (US); The Board of Trustees of the Leland Stanford Junior University, Stanford, CA (US)

(72) Inventors: Shan Xiang Wang, Palo Alto, CA (US); Viswam Siva Nair, Menlo Park, CA (US); Heng Yu, Campbell, CA (US); Michael J. Beggs, San Jose, CA (US); Luis Carbonell, Huntington Beach, CA (US)

(73) Assignees: Mag Array, Inc., Milpitas, CA (US); The Board of Trustees of the Leland Stanford Junior University, Stanford, CA (US)

( * ) Notice: Subject to any disclaimer, the term of this patent is extended or adjusted under 35 U.S.C. 154(b) by 110 days.

(21) Appl. No.: 16/125,432

(22) Filed: Sep. 7, 2018

(65) Prior Publication Data

US 2019/0107540 A1     Apr. 11, 2019

Related U.S. Application Data

(62) Division of application No. 15/266,848, filed on Sep. 15, 2016, now Pat. No. 10,101,330.

(60) Provisional application No. 62/305,333, filed on Mar. 8, 2016.

(51) Int. Cl.
G01N 33/574     (2006.01)

(52) U.S. Cl.
CPC . *G01N 33/57423* (2013.01); *G01N 33/57488* (2013.01)

(58) Field of Classification Search
CPC .................. G01N 33/577; C12Q 2600/112
See application file for complete search history.

(56) References Cited

U.S. PATENT DOCUMENTS

| 7,597,890 | B2 | 10/2009 | Chinnaiyan et al. |
| 7,906,345 | B2 | 5/2011 | Wang et al. |
| 9,151,763 | B2 | 10/2015 | Osterfeld et al. |
| 9,164,100 | B2 | 10/2015 | Osterfeld et al. |
| 9,506,919 | B2 | 11/2016 | Gaster et al. |
| 2009/0104707 | A1 | 4/2009 | Wang et al. |
| 2011/0027901 | A1 | 2/2011 | Gaster et al. |
| 2015/0377893 | A1 | 12/2015 | Osterfeld et al. |
| 2017/0261509 | A1 | 9/2017 | Wang et al. |

FOREIGN PATENT DOCUMENTS

| WO | WO 2002/073204 | 9/2002 |
| WO | WO 2005/047864 | 5/2005 |
| WO | WO 2007/076439 | 7/2007 |
| WO | WO 2009/067546 | 5/2009 |
| WO | WO 2010/027903 | 3/2010 |
| WO | WO 2015/187855 | 12/2015 |

OTHER PUBLICATIONS

Jumper et al. (2004) "Determination of the serum matrix metalloproteinase-9 (MMP-9) and tissue inhibitor of matrix metalloproteinase-1 (TIMP-1) in patients non-small-cell lung cancer prior to treatment," Respiratory Medicine 98(2): 173-177.
Qui et al. (2008) "Occurrence of Autoantibodies to Annexin I, 14-3-3 Theta and LAMR1 in Prediagnostic Lung Cancer Sera," Journal of Clinical Oncology 26(31): 5060-5066.
Sin et al. (2013) "Pro-Surfactant Protein B as a Biomarker for Lung Cancer Prediction," Journal of Clinical Oncology 31(36): 4536-4543.
Taguchi et al. (2011) "Lung Cancer Signatures in Plasma Based on Proteome Profiling of Mouse Tumor Models," Cancer Cell 20(3): 289-299.
Bettegowda et al. (2014) "Detrction of Circulating Tumor DNA in Early- and Late-Stage Human Malignancies," Sci. Transl. Med. 6(224): 1-25 (224ra24).
"Anti-dsDNA Antibodies", Wikipedia, https://en.wikipedia.org/wiki/Anti-dsDNA_antibodies (accessed online Oct. 1, 2020), 8 pages.
Li et al., (2019) "Applying Circulating Tumor DNA Methylation in the Diagnosis of Lung Cancer", Precision Clinical Medicine, 2(1), 45-56.
Spaks et al. (2015) "Diagnostic Value of Circulating CXC Chemokines in Non-Small Cell Lung Cancer", Anticancer Research 35:6979-6984.

*Primary Examiner* — Prema M Mertz
(74) *Attorney, Agent, or Firm* — Rudy J. Ng; Brian Davy; Bozicevic, Field & Francis LLP

(57) ABSTRACT

Aspects of the present disclosure include methods of producing a circulating analyte profile of a subject. The methods include contacting a blood sample from a subject with a panel of probes for specific binding to analytes, and detecting the presence or absence of binding of the analytes to probes of the panel of probes. Also provided are sensor devices including a panel of capture probes and useful, e.g., for practicing the methods of the present disclosure.

7 Claims, 9 Drawing Sheets

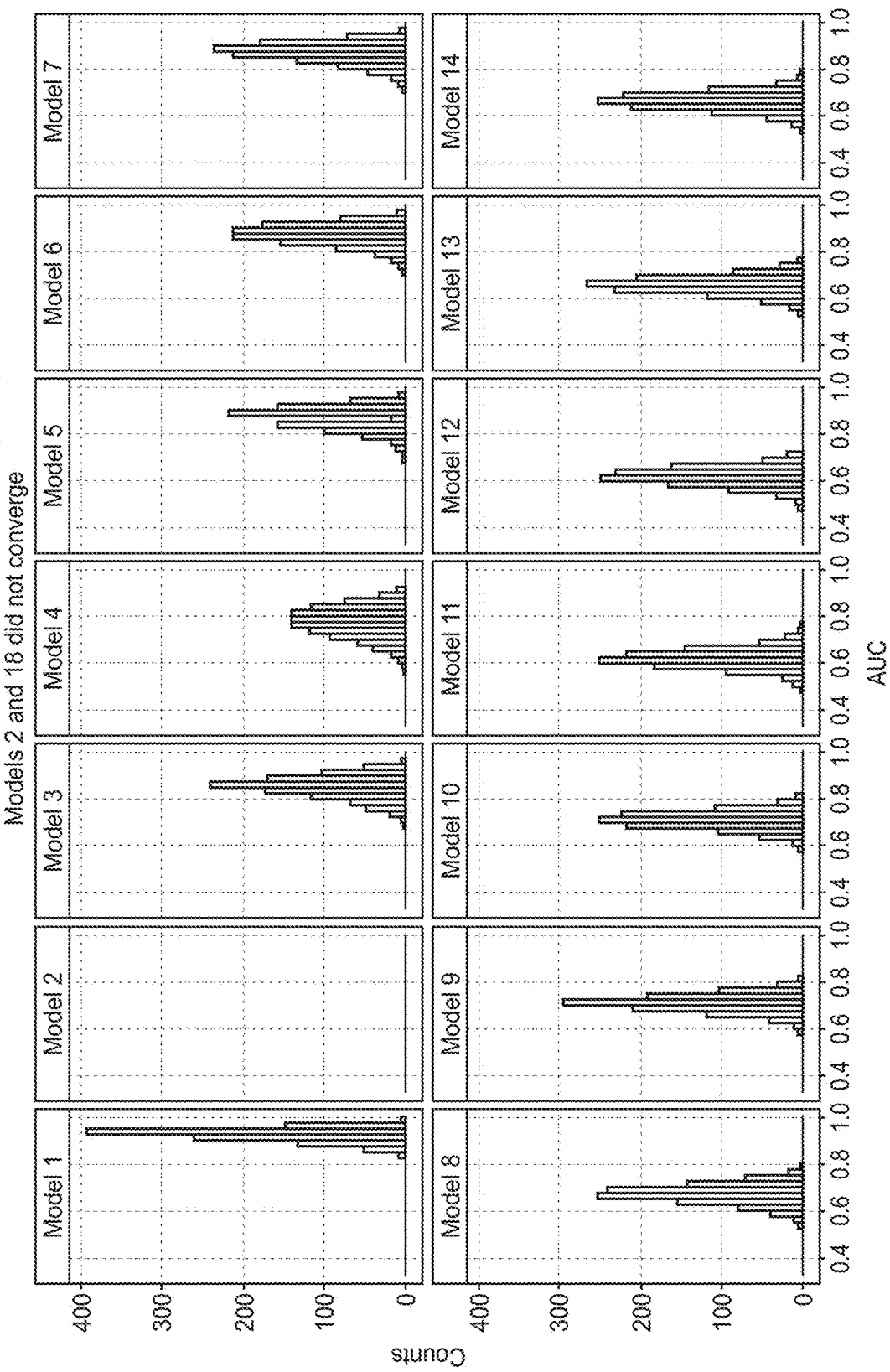

Table 1. Logistic Regression Models Sorted by AUC Rank.

| Model # | Cohort | Outcome | Age | Sex | Cancer Hx | Nodule_ location | Nodule_ size | Nodule_ border | SUV max | P1 AGR2.1 | P3 EGFR | P6 ProSB | P7 TIMP1 | A1 14.3.3 Theta | A2 ANGP TL3 | A4 LAM R1 | Smoking 3 level | Smoking Never vs. Current | Smoking Never vs. Ever | Mean AUC (95% CI) | AUC rank |
|---|---|---|---|---|---|---|---|---|---|---|---|---|---|---|---|---|---|---|---|---|---|
| 1 | Current Smoker | Diagnosis | X | X |  | X |  |  | X | X |  |  | X | X | X |  |  |  |  | 0.95 (0.88, 0.99) | 1 |
| 17 | Current Smoker | Diagnosis | X | X | X | X |  |  |  |  | X |  | X | X | X |  |  |  |  | 0.94 (0.87, 0.99) | 2 |
| 21 | Current Smoker | Diagnosis | X | X | X | X | X | X |  |  |  |  | X |  | X | X |  |  |  | 0.93 (0.84, 0.99) | 3 |
| 24 | Current Smoker | Diagnosis | X | X | X |  |  |  |  | X | X | X | X | X | X | X |  |  |  | 0.91 (0.82, 0.97) | 4 |
| 6 | Current Smoker | Diagnosis | X | X |  |  |  |  |  |  | X | X | X | X | X |  |  |  |  | 0.89 (0.80, 0.97) | 5 |
| 5 | Current Smoker | Diagnosis | X | X | X | X | X | X |  |  |  |  | X | X | X |  |  |  |  | 0.89 (0.79, 0.97) | 6 |
| 7 | Current Smoker | Diagnosis | X | X | X |  |  |  |  |  |  |  | X | X | X | X |  |  |  | 0.88 (0.78, 0.97) | 7 |
| 23 | Current Smoker | Diagnosis | X |  | X |  |  |  |  | X |  |  |  |  |  |  |  |  |  | 0.88 (0.78, 0.96) | 8 |
| 19 | Current Smoker | Diagnosis | X | X |  |  |  |  |  |  | X |  | X | X | X | X |  |  |  | 0.88 (0.78, 0.96) | 9 |
| 22 | Current Smoker | Diagnosis | X | X | X |  | X |  |  |  |  |  | X |  |  |  |  |  |  | 0.88 (0.78, 0.96) | 10 |
| 3 | Current Smoker | Diagnosis | X |  |  |  |  |  |  |  | X | X | X | X | X | X |  |  |  | 0.88 (0.77, 0.96) | 11 |
| 4 (VN Model) | Current Smoker | Diagnosis | X | X | X | X | X | X |  |  |  |  |  |  |  |  |  |  |  | 0.80 (0.66, 0.91) | 12 |
| 20 | Current Smoker | Diagnosis | X | X | X |  |  |  |  |  |  |  | X |  |  |  |  |  |  | 0.78 (0.63, 0.90) | 13 |
| 28 | All | Diagnosis | X | X |  |  |  |  |  |  |  |  | X | X | X | X |  |  | X | 0.76 (0.69, 0.82) | 14 |
| 26 | All | Diagnosis | X | X |  |  |  |  |  |  |  |  | X | X | X | X | X |  |  | 0.75 (0.69, 0.82) | 15 |
| 25 | All | Diagnosis | X | X |  | X | X |  |  |  |  |  | X | X | X | X |  |  |  | 0.75 (0.67, 0.81) | 16 |
| 10 | All | Smoking | X | X |  |  |  |  |  |  | X | X | X | X | X |  |  |  |  | 0.73 (0.66, 0.81) | 17 |
| 9 | All | Smoking | X |  |  |  |  |  |  |  | X | X | X | X | X |  |  |  |  | 0.73 (0.66, 0.80) | 18 |
| 8 | All | Smoking |  |  |  |  |  |  |  |  | X | X | X | X | X |  |  |  |  | 0.70 (0.61, 0.77) | 19 |
| 14 | All | Diagnosis | X | X | X | X | X |  |  |  | X | X | X | X | X |  |  |  |  | 0.69 (0.61, 0.76) | 20 |
| 13 | All | Diagnosis | X | X | X | X | X | X |  |  | X | X | X | X | X |  |  |  |  | 0.68 (0.61, 0.76) | 21 |
| 15 | All | Diagnosis | X | X | X | X |  |  |  |  | X | X | X | X | X |  |  |  |  | 0.65 (0.57, 0.72) | 22 |
| 16 | All | Diagnosis | X | X | X |  |  |  |  |  | X | X | X | X | X |  |  |  |  | 0.65 (0.57, 0.72) | 23 |
| 12 | All | Diagnosis | X | X |  |  |  |  |  |  | X | X | X | X | X |  |  |  |  | 0.64 (0.57, 0.72) | 24 |
| 11 | All | Diagnosis | X | X |  |  |  |  |  |  | X | X | X | X | X |  |  |  |  | 0.64 (0.56, 0.73) | 25 |
| 27 | All | Diagnosis | X | X | X |  |  |  |  |  |  |  |  |  |  |  |  | X |  | 0.69 (0.61, 0.76) | 26 |
| 2 | Current Smoker | Diagnosis | X | X |  | X | X | X |  | X |  |  |  |  |  |  |  |  |  | 0.65 (0.57, 0.72) | 27 |
| 18 | Current Smoker | Diagnosis | X | X |  | X | X |  |  |  |  |  |  |  |  |  |  |  |  | 0.52 (0.44, 0.60) | 28 |

X These variables (age, sex, P3, P6) are used together as a single smoking classifier factor in the indicated models.

FIG. 8

Table 2. Coefficients for logistic regression predictive models 1, 6, 7, and 17

| Model | (Intercept) | age | sex_code Male | CancerHx Yes | SUV max | Nodule Location LUL | Nodule Location RLL | Nodule Location RML | Nodule Location RUL | log P1 AGR2.1 | log P3 EGFR | log P6 ProSB | log P7 TIMP1 | log A1 14.3.3 Theta | log A2 ANGPTL3 | log A4 LAMR1 |
|---|---|---|---|---|---|---|---|---|---|---|---|---|---|---|---|---|
| 1 | -53.6852 | -0.006 | | | 0.577 | 2.557 | -2.217 | -1.120 | 1.555 | 0.102 | | | 6.480 | | 1.466 | |
| 6 | -51.2475 | 0.093 | 1.084 | | | | | | | | 0.260 | -1.055 | 5.533 | 0.132 | 1.567 | 0.839 |
| 7 | -53.0136 | 0.092 | 1.202 | -0.546 | | | | | | | 0.485 | -1.075 | 5.626 | 0.084 | 1.558 | 0.897 |
| 17 | -63.9109 | 0.138 | 1.952 | -0.951 | | 0.882 | -3.219 | 0.457 | 1.059 | | -0.050 | -1.111 | 6.399 | 0.283 | 1.639 | 2.058 |

FIG. 9

PROTEIN AND AUTOANTIBODY BIOMARKERS FOR THE DIAGNOSIS AND TREATMENT OF LUNG CANCER

CROSS REFERENCE TO RELATED APPLICATIONS

This application claims priority pursuant to 35 U.S.C. § 119(e) to the filing date of U.S. Provisional Patent Application Ser. No. 62/305,333, filed Mar. 8, 2016, the disclosure of which is incorporated herein by reference in its entirety.

REFERENCE TO GOVERNMENT SUPPORT

This invention was made with government support under Grant Numbers U54CA151459, U54 CA199075, and R44 CA165296 awarded by the National Institutes of Health. The government has certain rights in the invention.

INTRODUCTION

Lung cancer is the second most prevalent cancer—and the most lethal—in the U.S. For the most common type of lung cancer, non-small cell lung cancer (NSCLC), the five-year survival rate is 70-80% for stage I disease without nodal or distant metastasis, but only 5-15% for advanced stage IV (distant) disease. Current clinical algorithms and imaging modalities are adequate for diagnosis of later stages, but they remain imperfect for defining benign from malignant disease, particularly in the early development of NSCLC. Invasive tissue biopsies can be risky for initial diagnosis, therefore a "liquid biopsy" approach is a safer and potentially more cost-effective approach if assays for measuring cancer biomarkers in peripheral blood can be developed and validated for clinical use. Earlier diagnosis of lung cancer has the potential to save more patient lives.

Proteomics has been an intense area of study for biomarker discovery over the past 15 years with few commercialized platforms to date. Some advances have been made in protein tumor biomarker discovery in parallel with technology development. For example, enzyme-linked immunosorbent assay (ELISA) and mass spectrometry (MS) based assays can be used to measure panels of antigen biomarkers and autoantibodies to tumor-associated antigens.

Other cancer markers have shown promise, such as putative circulating tumor cells (CTCs), which are present in stage I NSCLC. However, false positive signals may occur from circulating epithelial cells (CECs) that are not cancer cells. Finally, circulating tumor DNA (ct-DNA) may have some utility in lung cancer diagnostics and therapy monitoring, although the technology is limited to specific somatic mutations that may not be specific to lung cancer and the sensitivity for detection in early disease may not be sufficient.

Obtaining sensitive and precise measurements of specific biomarkers for lung cancer is desirable for analyzing protein levels in blood samples. For example, ultrasensitive, multiplex in vitro diagnostics suitable for use with real-world samples are needed in the field of cancer diagnostics.

SUMMARY

Aspects of the present disclosure include methods of producing a circulating analyte profile of a subject. The methods include contacting a blood sample from a subject with a panel of probes for specific binding to analytes, and detecting the presence or absence of binding of the analytes to probes of the panel of probes. Also provided are sensor devices including a panel of capture probes and useful, e.g., for practicing the methods of the present disclosure.

BRIEF DESCRIPTION OF THE FIGURES

FIG. 1 (panel b) shows a four-plex autoantibody assay of plasma samples with magneto-nanosensors. Shown are real-time binding curves observed during the assay, with error bars denoting intra-assay standard deviation of each analyte signal. The reference median signal was from BSA-coated sensors, indicating specificity of the assay. FIG. 1 (panel c) shows a graph of a comparison of EGFR standard curves between the magnetic sensor and an ELISA assay. The magnetic sensor of the present disclosure had significantly better sensitivity for detecting EGFR.

FIG. 8 shows a table (Table 1) of logistic regression models sorted by AUC rank, according to embodiments of the present disclosure.

FIG. 9 shows a table (Table 2) of coefficients for logistic regression predictive Models 1, 6, 7 and 17, according to embodiments of the present disclosure.

DETAILED DESCRIPTION

Figure 1:
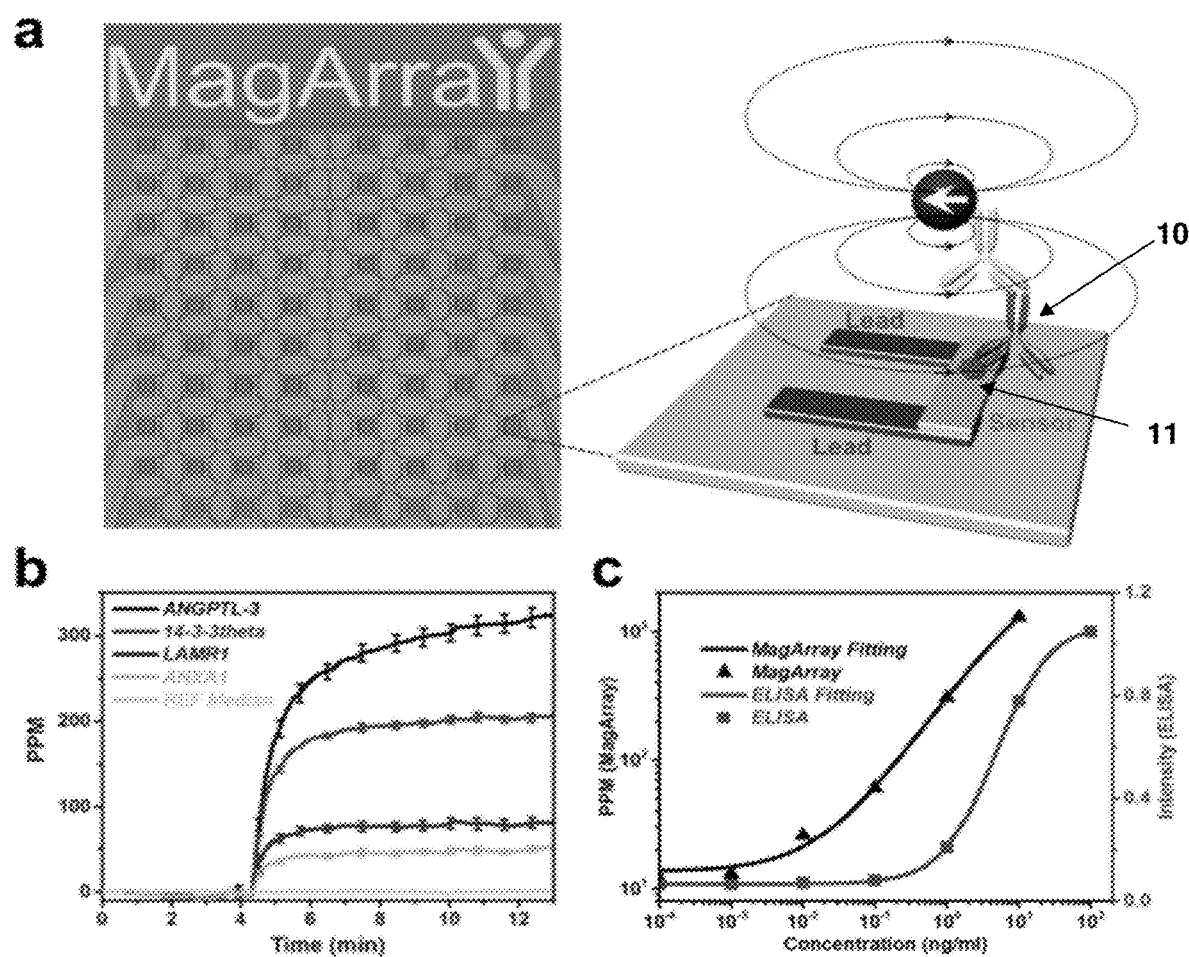
FIG. 1 (panel a) shows a magneto-nanosensor chip with 80 sensors, each of which can be functionalized to detect a unique autoantibody analyte 10 with a known capture antigen 11 pre-immobilized on the sensor surface, according to embodiments of the present disclosure.

Provided are methods of producing a circulating analyte profile of a subject. The methods include contacting a blood sample from a subject with a panel of probes for specific binding to analytes, and detecting the presence or absence of binding of the analytes to probes of the panel of probes. Also provided are sensor devices including a panel of capture probes and useful, e.g., for practicing the methods of the present disclosure.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed, to the extent that such combinations embrace operable processes and/or devices/systems/kits. In addition, all sub-combinations listed in the embodiments describing such variables are also specifically embraced by the present invention and are disclosed herein just as if each and every such sub-combination of chemical groups was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods

Aspects of the present disclosure include methods of producing a circulating analyte profile of a subject. The methods include contacting a blood sample from a subject with a panel of probes for specific binding to analytes, and detecting the presence or absence of binding of the analytes to probes of the panel of probes. In certain aspects, the detecting includes quantifying detected analytes.

The circulating analyte profile may be produced from a blood sample (e.g., a whole blood sample, a plasma sample, or a serum sample) obtained from any of a variety of subjects. Generally, such subjects are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some embodiments, the circulating analyte profile is produced from a blood sample obtained from a human subject.

A probe of the panel of probes can be any molecule that specifically binds to an analyte of interest. Analytes of interest include, but are not limited to, proteins (including non-antibody proteins, antibody proteins, etc.), nucleic acids (e.g., tumor DNA or RNA), and cells (e.g., circulating tumor cells). The probes of the panel of probes may be selected depending on the nature of the analytes to be detected. For example, if one of the two or more analytes is a protein (e.g., a non-antibody protein or antibody protein), an antibody, ligand, or the like that specifically binds that protein may be employed as a probe in the panel of probes. If one of the two or more analytes is an antibody, the corresponding antigen for that antibody may be employed as a probe in the panel of probes. If one of the two or more analytes is a nucleic acid, a nucleic acid sufficiently complementary to a unique region of that nucleic acid to achieve specific binding under the desired contacting conditions may be employed as a probe in the panel of probes, for example. Proteins (e.g., nucleic acid binding proteins, antibodies, and the like) may also be employed for binding to nucleic acid analytes.

The term "binding" refers to a direct association between two molecules, due to, for example, covalent, electrostatic, hydrophobic, ionic and/or hydrogen-bond interactions. The probes of the panel of probes bind specifically to their corresponding analytes. Non-specific binding (NSB) typically refers to the binding of an antibody to something other than its homologous antigen such as various other antigens in the sample. Under certain assay conditions, NSB would refer to binding with an affinity of less than about $10^{-7}$ M, e.g., binding with an affinity of $10^{-6}$ M, $10^{-5}$ M, $10^{-4}$ M, etc.

The panel of probes includes a suitable number of probes for specific binding to the number of unique circulating analytes of interest. According to certain embodiments, the panel of probes includes a suitable number of probes for specific binding to from 2 to 5 analytes, from 6 to 10 analytes, from 10 to 15 analytes, from 15 to 20 analytes, from 20 to 25 analytes, from 25 to 30 analytes, from 30 to 35 analytes, from 35 to 40 analytes, from 40 to 45 analytes, from 45 to 50 analytes, from 50 to 60 analytes, from 60 to 70 analytes, from 70 to 80 analytes, from 80 to 90 analytes, from 90 to 100 analytes, from 100-200 analytes, from 200 to 300 analytes, from 300 to 400 analytes, from 400 to 500 analytes, or from 500 to 1000 analytes.

In certain aspects, the panel of probes includes probes for specific binding to two or more unique circulating analytes of interest, which panel includes probes for specific binding to 1000 or fewer, 500 or fewer, 400 or fewer, 300 or fewer, 200 or fewer, 100 or fewer, 75 or fewer, 50 or fewer, 40 or fewer, 30 or fewer, 25 or fewer, 20 or fewer, 15 or fewer, 10 or fewer, 9 or fewer, 8 or fewer, 7 or fewer, 6 or fewer, 5 or fewer, 4 or fewer, 3, or 2 unique circulating analytes of interest.

According to certain embodiments, the panel of probes includes probes for specific binding to two or more circulating analytes selected from tissue inhibitor of metalloproteinase 1 (TIMP1), anti-angiopoietin-like protein 3 antibody (anti-ANGPTL3), epidermal growth factor receptor (EGFR), pro-surfactant protein B (ProSB), anti-14-3-3 protein theta antibody (anti-YWHAQ), anti-laminin alpha 1 antibody (anti-LAMR1), human epididymis protein 4 (HE4), anterior gradient protein 2 (AGR2), chromogranin A (CHGA), leucine-rich alpha-2-glycoprotein 1 (LRG1), anti-annexin 1 antibody (anti-ANXA1), anti-ubiquilin 1 antibody (anti-UBQLN1), interleukin 6 (IL6), interleukin 8 (IL8), chemokine (C-X-C motif) ligand 2 (CXCL2), defensin, beta 1 (DEFB1), fibroblast growth factor 2 (FGF2), cluster of differentiation 97 (CD97), pro-platelet basic protein (PPBP), procalcitonin (PCT), receptor for advanced glycation end-products (RAGE), S100 calcium-binding protein A4 (S100A4), S100 calcium-binding protein A8/A9 complex (S100A8/A9), osteopontin (OPN), and any combination thereof.

In certain aspects, the panel of probes includes probes for specific binding to 2, 3, 4, 5, 6, 7, 8, 9, 10, 11, 12, 13, 14, 15, 16, 17, 18, 19, 20, 21, 22, 23, or each of TIMP1, anti-ANGPTL3, EGFR, ProSB, anti-YWHAQ, anti-LAMR1, HE4, AGR2, CHGA, LRG1, anti-ANXA1, anti-UBQLN1, IL6, IL8, CXCL2, DEFB1, FGF2, CD97, PPBP, PCT, RAGE, S100A4, S100A8/A9, and OPN, in any desired combination. According to certain embodiments, such a panel of probes includes probes for binding to 50 or fewer, 40 or fewer, 30 or fewer, 25 or fewer, 20 or fewer, 15 or fewer, 10 or fewer, 9 or fewer, 8 or fewer, 7 or fewer, 6 or fewer, 5 or fewer, 4 or fewer, 3, or 2 unique analytes.

According to certain embodiments, the panel of probes includes probes for specific binding to 2, 3, 4, 5 or each of TIMP1, anti-ANGPTL3, EGFR, ProSB, anti-YWHAQ, and anti-LAMR1. Such a panel may include one or more probes for specific binding to one or more additional unique circulating analytes (e.g., 20 or fewer additional analytes). The additional analytes may be selected from HE4, AGR2, CHGA, LRG1, anti-ANXA1, anti-UBQLN1, IL6, IL8, CXCL2, DEFB1, FGF2, CD97, PPBP, PCT, RAGE, S100A4, S100A8/A9, OPN, and any combination thereof. The panel of probes may include probes for binding to 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, or each of the additional analytes. Such a panel of probes may include probes for binding to 50 or fewer, 40 or fewer, 30 or fewer, 25 or fewer, 20 or fewer, 15 or fewer, 10 or fewer, 9 or fewer, 8 or fewer, 7 or fewer, 6 or fewer, 5 or fewer, 4, or 3 unique analytes.

In certain aspects, the panel of probes includes one or more probes for binding to one or more types of circulating cells. Circulating cells of interest include, but are not limited to, circulating tumor cells and circulating stem cells. By "circulating tumor cell" (CTC) is meant a cancer cell that is exfoliated from a solid tumor of a subject and is found in the subject's circulation, e.g., the subject's peripheral blood, bone marrow, and/or the like. A probe may bind to a circulating cell (e.g., a CTC) by virtue of the probe having specificity for a known cell surface molecule (e.g., a receptor, adhesion molecule, etc.) expressed by the circulating cell of interest. When the circulating cell is a CTC, the probe (e.g., an antibody probe) may specifically bind to a tumor-associated or tumor-specific antigen expressed by the CTC. By "tumor-associated antigen" is meant a cell surface molecule expressed on malignant cells with limited expression on cells of normal tissues, a cell surface molecule expressed at much higher density on malignant versus normal cells, or a cell surface molecule that is developmentally expressed. A "tumor-specific antigen" is an antigen present on the surface of malignant cells and not present on non-malignant cells. The types of CTCs that may be bound by probes of the panel of the probes may vary, e.g., depending on the type of solid tumor from which the CTC sloughed off. In certain aspects, the panel of the probes may include probes for specific binding to CTCs, which probes specifically bind to epithelial cell adhesion molecule (EpCAM) and/or any other useful cell surface CTC molecules.

According to certain embodiments, the panel of probes includes one or more probes for binding to one or more types of circulating nucleic acids. Circulating nucleic acids of interest include circulating double or single-stranded DNA, circulating double or single-stranded RNA, circulating DNA-RNA hybrids, etc. In certain aspects, the panel includes one or more probes for specific binding to one or more circulating tumor DNAs (ctDNA). Dying tumor cells release small pieces of their DNA into the bloodstream, and the amount/concentration of ctDNA in blood often increases as the cancer stage increases. According to certain embodiments, the panel of probes includes a probe for specific binding to a ctDNA that includes a somatic mutation known to be associated with (or specific to) a tumor type of interest. Clinically relevant ctDNAs include those described in Bettegowda et al. (2014) Sci. Transl. Med. 6(224): 224ra24.

The methods of the present disclosure include detecting the presence or absence of binding of analytes of the two or more analytes to probes of the panel of probes, to produce a circulating analyte profile of the subject. In certain aspects, the detecting includes quantifying detected analytes. Any of a variety of suitable assay formats and detection approaches may be employed. In certain aspects, the probes of the panel of probes may be attached directly or indirectly to a solid support, such as a bead (e.g., a microparticle, nanoparticle, or the like) or a substantially flat solid support/substrate. According to certain embodiments, the probes may be attached to a solid support as an array. For example, the panel of probes may be a panel of probes provided as an addressable probe array.

In certain aspects, detecting the presence or absence of binding of analytes of the two or more analytes to probes of the panel of probes is carried out using a sandwich assay. For example, the probes of the panel of probes may be attached to a solid surface (e.g., as an array) for capturing analytes of the two or more analytes, and detection reagents are added that bind (e.g., specifically bind) to the two or more analytes (if present in the blood sample) at sites of the analytes not bound by the probes. In certain aspects, a detection reagent is a detection antibody that binds to an epitope of the analyte that is different from the binding site (e.g., epitope) to which the probe of the panel of probes binds. As a result, the analyte is "sandwiched" between the probe and the detection reagent. The detection reagents may include detectable labels such that detecting the presence or absence of binding of analytes of the two or more analytes to probes of the panel of probes involves detecting the labels of the detection reagents. According to certain embodiments, a secondary detection reagent is employed. Suitable secondary reagents include labeled secondary antibodies (e.g., fluorescently labeled antibodies, magnetic labeled antibodies, etc.), secondary antibodies linked to an enzyme that catalyzes the conversion of a substrate to a detectable product, and the like. Additional details and design considerations for sandwich and other assays that find use in practicing the methods of the present disclosure are described, e.g., in Cox et al. (2014) Immunoassay Methods, Eli Lilly & Company and the National Center for Advancing Translational Sciences.

In certain aspects, a detection reagent that binds to the analyte bound by the probe is an antibody. Such a detection reagent may be a modified antibody. The modified antibody may be configured to specifically bind to the analyte of interest and may also include one or more additional members of a specific binding pair. The one or more members of a specific binding pair may be configured to specifically bind to a complementary member of the specific binding pair. In certain instances, the complementary member of the specific binding pair is bound to a magnetic label, e.g., when a magnetic sensor device is employed to carry out the method. An antibody detection reagent may be modified to include biotin, which biotin will specifically bind to streptavidin, e.g., a magnetic label modified to include streptavidin. As such, in certain aspects, the detection reagent specifically binds to the analyte (e.g., through an antibody-antigen interaction) and specifically binds to a label (e.g., a magnetic label) via a selected interaction (e.g., through a streptavidin-biotin interaction). The detection reagent may be configured to bind to the analyte and a label (e.g., a magnetic label). Stated another way, the detection reagent may be configured such that specific binding of the analyte to the detection reagent does not significantly interfere with the ability of the detection reagent to specifically bind to a label. Similarly, the detection reagent may be configured such that specific binding of the label to the detection reagent does not significantly interfere with the ability of the detection reagent to bind to the analyte.

The presence of the two or more analytes in the blood sample may be determined qualitatively or quantitatively. Qualitative determination includes determinations in which a simple yes/no result with respect to the presence of an analyte in the sample is provided to a user. Quantitative determination includes both semi-quantitative determinations in which a rough scale result, e.g., low, medium, high, is provided to a user regarding the amount of analyte in the sample and fine scale results in which a precise measurement of the concentration of the analyte is provided to the user.

Magnetic Sensor-Based Methods

According to certain embodiments, the methods of the present disclosure are carried out using a magnetic sensor device. For example, the panel of probes may be arrayed (e.g., provided as an addressable probe array) on a magnetic sensor chip of a magnetic sensor device. The magnetic sensor device may have two or more magnetic sensors having panels of probes (e.g., identical or different arrays of capture probes) attached to the surface thereof. Any of the panels of probes described above may be employed. In certain aspects, each of the two or more magnetic sensors having panels of capture probes attached to the surface thereof includes capture probes for binding to the same two or more circulating analytes.

Methods of the present disclosure that employ a magnetic sensor device may include contacting the magnetic sensor device having the panel of capture probes attached to the surface thereof (e.g., arrayed) with the blood sample and detecting signals indicating the binding of the two or more analytes (if present in the blood sample) to the panel of capture probes. In some cases, the magnetic sensor device includes sensors configured to detect the presence of nearby magnetic labels without any direct physical contact between the magnetic sensor and a magnetic label. A magnetic label may be bound, either directly or indirectly, to an analyte, which in turn may be bound, either directly or indirectly, to the magnetic sensor. If the bound magnetic label is positioned within the detection range of the magnetic sensor, then the magnetic sensor may provide a signal indicating the presence of the bound magnetic label, and thus indicating the presence of the analyte.

In certain aspects, the methods of the present disclosure are performed using a sandwich assay in which the panel of probes is attached to a surface of a sensing region of the magnetic sensor device. The blood sample is dispensed on the sensing region to contact the blood sample with the panel of probes under conditions in which analytes of the two or more analytes (if present in the blood sample) bind to their respective probes. With or without washing, detection reagents may be added that bind to analytes of the two or more analytes which are bound to the probes of the panel of probes. In some instances, the detection reagents are directly bound to a magnetic label. In other aspects, the detection reagents are not directly bound to a magnetic label, but rather secondary magnetically labeled detection reagents that bind to the detection reagents are employed. For example, a detection reagent may specifically bind to the analyte (e.g., through an antibody-antigen interaction) and specifically bind to a magnetic label via a selected interaction (e.g., through a streptavidin-biotin interaction). Binding of the detection reagent(s) to a surface-bound analyte positions the magnetic label within the detection range of the magnetic sensor, such that a detectable signal indicative of the presence of the analyte is induced in the magnetic sensor.

In certain embodiments, an electrical signal is generated in response to a magnetic label in proximity to a surface of the magnetic sensor. For example, the magnetic sensor may be configured to detect changes in the resistance of the magnetic sensor induced by changes in the local magnetic field. In some cases, binding of a magnetic label (e.g., a magnetic nanoparticle label) in close proximity to the magnetic sensor, induces a detectable change in the resistance of the magnetic sensor. For instance, in the presence of an applied external magnetic field, the magnetic labels near the magnetic sensor may be magnetized. The local magnetic field of the magnetized magnetic labels may induce a detectable change in the resistance of the underlying magnetic sensor. Thus, the presence of the magnetic labels can be detected by detecting changes in the resistance of the magnetic sensor. As will be described in further detail below, a magnetic sensor device that finds use in practicing the methods of the present disclosure may include a magnetoresistive element. Non-limiting examples of magnetoresistive elements which may be employed include spin valve magnetoresistive elements and magnetic tunnel junction (MTJ) magnetoresistive elements.

In some instances, the methods are wash-free methods of evaluating the presence of the two or more analytes in the blood sample. By "wash-free" is meant that no washing step is performed following reagent and/or blood sample contact with a magnetic sensor. As such, no step is performed during the assays of these embodiments in which unbound reagent (e.g., unbound magnetic labels) or unbound sample is removed from the magnetic sensor surface. Accordingly, while the methods may include sequential contact of one or more distinct reagents and/or samples to a magnetic sensor surface, at no point during the assay is the sample surface contacted with a fluid in a manner that removes unbound reagent or sample from the magnetic sensor surface. For example, in certain embodiments, no washing step is performed following contact of the magnetic sensor surface with the blood sample. In some cases, the method does not include a washing step following contact of the magnetic sensor surface with a magnetic label. In certain instances, no washing step is performed following contact of the magnetic sensor surface with a detection reagent.

In certain embodiments where a wash step is performed, the wash step does not substantially change the signals from the magnetic sensor. The wash step may not result in a substantial change in the signals from the magnetic sensor because, in some instances, unbound magnetic labels do not have a substantially detectable signal as described herein. For example, if a wash step is performed, in some cases, the wash step results in a signal change of 25% or less, such as 20% or less, or 15% or less, or 10% or less, or 5% or less, or 4% or less, or 3% or less, or 2% or less, or 1% or less, as compared to a signal obtained prior to the wash step. In some embodiments, the wash step results in a decrease in the signals from the magnetic sensor of 25% or less, such as 20% or less, or 15% or less, or 10% or less, or 5% or less, or 4% or less, or 3% or less, or 2% or less, or 1% or less.

Aspects of the methods may also include obtaining a real-time signal from the magnetic sensor device. By "real-time" is meant that a signal is observed as it is being produced. For example, a real-time signal is obtained from the moment of its initiation and is obtained continuously over a given period of time. Accordingly, certain embodiments include observing the evolution in real time of the signal associated with the occurrence of a binding interaction of interest (e.g., the binding of analytes of the two or more analytes of interest to the magnetic sensor and/or binding of a magnetic label to the analyte of interest). The real-time signal may include two or more data points obtained over a given period of time, where in certain embodiments the signal obtained is a continuous set of data points (e.g., in the form of a trace) obtained continuously over a given period of time of interest. The time period of interest may vary, ranging in some instances from 0.5 min to 60 min, such as 1 min to 30 min, including 1 min to 15 min, or 1 min to 10 min. For example, the time period may begin at the moment of initiation of the real-time signal and may continue until the sensor reaches a maximum or saturation level (e.g., where all the analyte binding sites on the sensor are occupied). For example, in some cases, the time period begins when the blood sample is contacted with the sensor. In some cases, the time period may begin prior to contacting the blood sample with the sensor, e.g., to record a baseline signal before contacting sample to the sensor. The number of data points in the signal may also vary, where in some instances, the number of data points is sufficient to provide a continuous stretch of data over the time course of the real-time signal. By "continuous" is meant that data points are obtained repeatedly with a repetition rate of 1 data point per minute or more, such as 2 data points per minute or more, including 5 data points per minute or more, or 10 data points per minute or more, or 30 data points per minute or more, or 60 data points per minute or more (e.g., 1 data point per second or more), or 2 data points per second or more, or 5 data points per second or more, or 10 data points per second or more, or 20 data points per second or more, or 50 data points per second or more, or 75 data points per second or more, or 100 data points per second or more.

A real-time signal may be a real-time analyte-specific signal. A real-time analyte-specific signal is a real-time signal as described above that is obtained only from a specific analyte of the two or more analytes of interest. In these embodiments, unbound analytes and unbound magnetic labels do not produce a detectable signal. As such, the real-time signal that is obtained is only from the specific magnetically-labeled analyte of interest bound to the magnetic sensor and substantially no signal is obtained from unbound magnetic labels or other reagents (e.g., analytes not specifically bound to the sensor).

In some embodiments, the signal is observed while the assay device is in a wet condition. By "wet" or "wet condition" is meant that the assay composition (e.g., an assay composition that includes the blood sample, a magnetic label, and one or more detection reagents) is still in contact with the surface of the magnetic sensor. As such, there is no need to perform any washing steps to remove the non-binding moieties that are not of interest or the excess unbound magnetic labels or capture probes. In certain embodiments, the use of magnetic labels and magnetic sensors, as described above, facilitates "wet" detection because the signal induced in the magnetic sensor by the magnetic label decreases as the distance between the magnetic label and the surface of the magnetic sensor increases. For example, the use of magnetic labels and magnetic sensors, as described above, may facilitate "wet" detection because the magnetic field generated by the magnetic labels decreases as the distance between the magnetic label and the surface of the magnetic sensor increases. In some instances, the magnetic field of the magnetic label bound to the surface-bound analyte significantly exceeds the magnetic field from the unbound magnetic labels dispersed in solution. For example, as described above, a real-time analyte-specific signal may be obtained only from the specific magnetically-labeled analyte of interest bound to the magnetic sensor and substantially no signal may be obtained from unbound magnetic labels dispersed in solution (e.g., not specifically bound to the sensor). The unbound magnetic labels dispersed in solution may be at a greater distance from the surface of the magnetic sensor and may be in Brownian motion, which may reduce the ability of the unbound magnetic labels to induce a detectable change in the resistance of the magnetic sensor. Unbound magnetic labels may also be suspended in solution, for example as a colloidal suspension (e.g., due to having a nanometer-scale size), which may reduce the ability of the unbound magnetic labels to induce a detectable change in the resistance of the magnetic sensor.

Magnetic labels that may be employed in various methods (e.g., as described herein) may vary, and include any type of label that induces a detectable signal in a magnetic sensor when the magnetic label is positioned near the surface of the magnetic sensor. Magnetic labels are labeling moieties that, when sufficiently associated with a magnetic sensor, are detectable by the magnetic sensor and cause the magnetic sensor to output a signal. For example, the presence of a magnetic label near the surface of a magnetic sensor may induce a detectable change in the magnetic sensor, such as, but not limited to, a change in resistance, conductance, inductance, impedance, etc. In some cases, the presence of a magnetic label near the surface of a magnetic sensor induces a detectable change in the resistance of the magnetic sensor. Magnetic labels of interest may be sufficiently associated with a magnetic sensor if the distance between the center of the magnetic label and the surface of the sensor is 1000 nm or less, such as 800 nm or less, such as 400 nm or less, including 100 nm or less, or 75 nm or less, or 50 nm or less, or 25 nm or less, or 10 nm or less.

In certain instances, the magnetic labels include one or more materials selected from paramagnetic, superparamagnetic, ferromagnetic, ferrimagnetic, antiferromagnetic materials, combinations thereof, and the like. For example, the magnetic labels may include superparamagnetic materials. In certain embodiments, the magnetic labels are configured to be nonmagnetic in the absence of an external magnetic field. By "nonmagnetic" is meant that the magnetization of a magnetic label is zero or averages to zero over a certain period of time. In some cases, the magnetic label may be nonmagnetic due to random flipping of the magnetization of the magnetic label over time. Magnetic labels that are configured to be nonmagnetic in the absence of an external magnetic field may facilitate the dispersion of the magnetic labels in solution because nonmagnetic labels do not normally agglomerate in the absence of an external magnetic field or even in the presence of a small magnetic field in which thermal energy is still dominant. In certain embodiments, the magnetic labels include superparamagnetic materials or synthetic antiferromagnetic materials. For instance, the magnetic labels may include two or more layers of antiferromagnetically-coupled ferromagnets.

In certain embodiments, the magnetic labels are high moment magnetic labels. The magnetic moment of a magnetic label is a measure of its tendency to align with an external magnetic field. By "high moment" is meant that the magnetic labels have a greater tendency to align with an external magnetic field. Magnetic labels with a high magnetic moment may facilitate the detection of the presence of the magnetic labels near the surface of the magnetic sensor because it is easier to induce the magnetization of the magnetic labels with an external magnetic field.

In certain embodiments, the magnetic labels include, but are not limited to, Co, Co alloys, ferrites, cobalt nitride, cobalt oxide, Co—Pd, Co—Pt, iron, iron oxides, iron alloys, Fe—Au, Fe—Cr, Fe—N, $Fe_3O_4$, Fe—Pd, Fe—Pt, Fe—Zr—Nb—B, Mn—N, Nd—Fe—B, Nd—Fe—B—Nb—Cu, Ni, Ni alloys, combinations thereof, and the like. Examples of high moment magnetic labels include, but are not limited to, Co, Fe or CoFe nanocrystals, which may be superparamagnetic at room temperature, and synthetic antiferromagnetic nanoparticles.

In some embodiments, the surface of the magnetic label is modified. In certain instances, the magnetic labels may be coated with a layer configured to facilitate stable association of the magnetic label with one member of a binding pair, as described above. For example, the magnetic label may be coated with a layer of gold, a layer of poly-L-lysine modified glass, dextran, and the like. In certain embodiments, the magnetic labels include one or more iron oxide cores imbedded in a dextran polymer. Additionally, the surface of the magnetic label may be modified with one or more surfactants. In some cases, the surfactants facilitate an increase in the water solubility of the magnetic labels. In certain embodiments, the surface of the magnetic labels is modified with a passivation layer. The passivation layer may facilitate the chemical stability of the magnetic labels in the assay conditions. For example, the magnetic labels may be coated with a passivation layer that includes gold, iron oxide, polymers (e.g., polymethylmethacrylate films), and the like.

In certain embodiments, the magnetic labels have a spherical shape. Alternatively, the magnetic labels can be disks, rods, coils, or fibers. In some cases, the size of the magnetic labels is such that the magnetic labels do not interfere with the binding interaction of interest. For example, the magnetic labels may be comparable to the size of the analyte and the capture probe, such that the magnetic labels do not interfere with the binding of the capture probe to the analyte. In some cases, the magnetic labels are magnetic nanoparticles, or contain multiple magnetic nanoparticles held together by a suitable binding agent. In some embodiments, the average diameter of the magnetic labels is from 5 nm to 250 nm, such as from 5 nm to 150 nm, including from 10 nm to 100 nm, for example from 25 nm to 75 nm. For example, magnetic labels having an average diameter of 5 nm, 10 nm, 20 nm, 25 nm, 30 nm, 35 nm, 40 nm, 45 nm, 50 nm, 55 nm, 60 nm, 70 nm, 80 nm, 90 nm, or 100 nm, as well as magnetic labels having average diameters in ranges between any two of these values, may be used with the subject methods. In some instances, the magnetic labels have an average diameter of 50 nm.

Magnetic labels and their conjugation to biomolecules are further described in U.S. Ser. No. 12/234,506, filed Sep. 19, 2008, and entitled "Analyte Detection with Magnetic Sensors", the disclosure of which is hereby incorporated by reference in its entirety.

Diagnostics

The methods of the present disclosure may further include diagnosing the subject as having a disease or condition based on the circulating analyte profile. The diagnosing may include diagnosing the severity (e.g., stage) of the disease or condition, monitoring the disease or condition, monitoring a response of the disease or condition to a therapy, and/or the like.

According to certain embodiments, the disease or condition is cancer. By the subject having "cancer" is meant the subject includes cells exhibiting a neoplastic cellular phenotype, which may be characterized by one or more of, for example, abnormal cell growth, abnormal cellular proliferation, loss of density dependent growth inhibition, anchorage-independent growth potential, ability to promote tumor growth and/or development in an immunocompromised non-human animal model, and/or any appropriate indicator of cellular transformation. "Cancer cell" may be used interchangeably herein with "tumor cell", "malignant cell" or "cancerous cell", and encompasses cancer cells of a solid tumor, a semi-solid tumor, a primary tumor, a metastatic tumor, and the like. Cancers that may be diagnosed based on the circulating analyte profile include, but are not limited to, cancers of the colon, breast, lung, prostate, skin, liver, pancreas, brain, kidney, endometrium, cervix, ovary, thyroid, lymphatic system, and blood.

In certain aspects, the methods include diagnosing the subject as having stage I, stage II, stage III, or stage IV cancer based on the circulating analyte profile. For example, the methods may include diagnosing the subject as having stage I cancer or diagnosing the subject as having stage II cancer. Cancer staging is the process of determining how much cancer is in the body and where it is located. Staging describes the severity of the subject's cancer, which severity may relate to, e.g., the magnitude of the original (primary) tumor and the extent to which the cancer has spread in the body. Understanding the stage of the cancer facilitates the development of a prognosis and treatment plan for the subject.

Staging of the cancer may be according to the TNM Staging System developed as a tool for doctors to stage different types of cancer based on certain, standardized criteria. The "T" category of the TNM Staging System relates to the original (primary) tumor. The "N" category describes whether or not the cancer has reached nearby lymph nodes. The "M" category relates to whether distant metastases are present. Because each cancer type has its own classification system, letters and numbers do not always mean the same thing for every kind of cancer. Once the T, N, and M are determined, they are combined, and an overall stage of 0, I, II, III, IV is assigned. Sometimes these stages are subdivided as well, using letters such as IIIA and IIIB.

A diagnosis may be based solely on the circulating analyte profile, or may be based in part on the circulating analyte profile. In instances where the diagnosis is based in part on the circulating analyte profile, the diagnosis may further be based on a clinical assessment selected from clinical imaging, age, sex, cancer history, nodule location, nodule size, nodule border, SUV max, smoking status, and any combination thereof.

In certain aspects, the methods include diagnosing the subject as having lung cancer. According to some embodiments, the methods include diagnosing the subject as having non-small cell lung cancer (NSCLC), e.g., squamous cell carcinoma, adenocarcinoma (e.g., acinar, papillary and bronchoalveolar), large cell carcinoma (e.g., giant cell and clear cell), adenosquamous carcinoma, and undifferentiated carcinoma. In stage 0 NSCLC, the cancer has not spread beyond the inner lining of the lung. At stage I of NSCLC, the cancer is small and has not spread to the lymph nodes. Stage II NSCLC is characterized by spread of the cancer to lymph nodes near the original (primary) tumor. In stage III NSCLC, the cancer has spread to nearby tissue or to distant lymph nodes. Stage IV NSCLC is characterized by the spread of the cancer to other organs of the body, such as the other lung, brain, or liver.

According to certain embodiments, the subject for which the circulating analyte profile is produced is from a population having a high risk of lung cancer. A subject may be at a high risk for lung cancer due to a variety of genetic, behavioral and/or environmental factors. According to certain embodiments, the subject is from a population having a high risk of lung cancer due to the subject being a current smoker, being a past smoker (e.g., a past heavy smoker), or both. According to certain embodiments, the subject being from a population having a high risk of lung cancer means the subject is from 55 to 74 years of age, has a minimum smoking history of 30 pack-years or more (where a "pack-year" is equal to the number of cigarette packs smoked per day×the number of years smoked), currently smokes or quit smoking within the past 15 years, and are apparently disease-free at the time the circulating analyte profile is produced. For example, a past heavy smoker may have a smoking history of 30 pack-years or more.

In certain aspects, the subject for which the circulating analyte profile is produced has an indeterminate lung lesion (or "nodule"). In some instances, the indeterminate lung lesion is identified by chest x-ray, CT scan of the chest, MRI of the chest, positron emission tomography (PET) scan of the chest, or other suitable imaging approach. The indeterminate lesion may be benign (non-cancer) and caused by scarring, inflammation, infection, or the like. In other instances, the lesion may be a lung cancer (e.g., an early lung cancer) or a cancer that has spread to the lung from another cancer in the body.

According to certain embodiments, the subject for which the circulating analyte profile is produced is undergoing lung cancer therapy. According to such embodiments, the methods may further include predicting, monitoring, or both, the therapeutic response of the subject to the lung cancer therapy based on the circulating analyte profile.

Treatment

The methods of the present disclosure may further include treating the subject for whom the circulating analyte profile is produced. In certain aspects, such methods include diagnosing the subject as having a disease or condition based on the circulating analyte profile, and the treatment step is performed subsequent to the diagnosis, e.g., based on the diagnosis. The treatment may include, e.g., administering to the subject a therapeutically effective amount of a pharmaceutical agent (e.g., a chemotherapeutic agent, a small molecule, a biologic (e.g., an antibody), engineered cells, and/or the like), radiation therapy, and/or the like. Alternatively, or additionally, the treatment may include removing from the subject all or part of a tissue (e.g., tumor tissue) or organ that contributes to (e.g., is responsible for) the disease or condition.

According to one embodiment, the subject is diagnosed as having lung cancer (e.g., non-small cell lung cancer) based on the circulating analyte profile, and the method includes treating the subject for the lung cancer. The treatment may include surgery to remove all or a portion of the cancer (e.g., by pneumonectomy, lobectomy, segmentectomy or wedge resection, sleeve resection, or the like); radiofrequency ablation (RFA) of all or a portion of the tumor; radiation therapy (e.g., external beam radiation therapy, brachytherapy (internal radiation therapy)); chemotherapy (e.g., by administering a therapeutically effective amount of cisplatin, carboplatin, paclitaxel, albumin-bound paclitaxel, docetaxel, gemcitabine, vinorelbine, irinotecan, etoposide, vinblastine, pemetrexed, or any combination thereof); targeted therapy (e.g., an antibody-based therapy, such as administration of bevacizumab and/or ramucirumab); immunotherapy (e.g., by administration of one or more immune checkpoint inhibitors, such as nivolumab and/or pembrolizumab); and any combination thereof. Palliative treatments may also be used to treat symptoms of the lung cancer.

Sensor Devices and Systems

As summarized above, aspects of the present disclosure include sensor devices (e.g., magnetic sensor devices). The sensor devices include a panel of probes for specific binding to two or more analytes. A sensor device of the present invention may include any of the panels of probes described hereinabove in the Methods section of the present disclosure. According to some embodiments, the sensor devices include a panel of capture probes provided as an addressable probe array (e.g., in a sensing region of the sensor device).

According to certain embodiments, the present sensor devices (e.g., magnetic sensor devices) include a panel of probes that includes probes for specific binding to two or more circulating analytes selected from tissue inhibitor of metalloproteinase 1 (TIMP1), anti-angiopoietin-like protein 3 antibody (anti-ANGPTL3), epidermal growth factor receptor (EGFR), pro-surfactant protein B (ProSB), anti-14-3-3 protein theta antibody (anti-YWHAQ), anti-laminin alpha 1 antibody (anti-LAMR1), human epididymis protein 4 (HE4), anterior gradient protein 2 (AGR2), chromogranin A (CHGA), leucine-rich alpha-2-glycoprotein 1 (LRG1), anti-annexin 1 antibody (anti-ANXA1), anti-ubiquilin 1 antibody (anti-UBQLN1), interleukin 6 (IL6), interleukin 8 (IL8), chemokine (C-X-C motif) ligand 2 (CXCL2), defensin, beta 1 (DEFB1), fibroblast growth factor 2 (FGF2), cluster of differentiation 97 (CD97), pro-platelet basic protein (PPBP), procalcitonin (PCT), receptor for advanced glycation endproducts (RAGE), S100 calcium-binding protein A4 (S100A4), S100 calcium-binding protein A8/A9 complex (S100A8/A9), osteopontin (OPN), and any combination thereof. In certain aspects, such a panel of probes includes probes for binding to 50 or fewer, 40 or fewer, 30 or fewer, 25 or fewer, 20 or fewer, 15 or fewer, 10 or fewer, 9 or fewer, 8 or fewer, 7 or fewer, 6 or fewer, 5 or fewer, 4 or fewer, 3, or 2 analytes.

In certain aspects, the sensor devices (e.g., magnetic sensor devices) of the present disclosure include a panel of probes that includes probes for specific binding to 2, 3, 4, 5, 6, 7, 8, 9, 10, 11, 12, 13, 14, 15, 16, 17, 18, 19, 20, 21, 22, 23, or each of TIMP1, anti-ANGPTL3, EGFR, ProSB, anti-YWHAQ, anti-LAMR1, HE4, AGR2, CHGA, LRG1, anti-ANXA1, anti-UBQLN1, IL6, IL8, CXCL2, DEFB1, FGF2, CD97, PPBP, PCT, RAGE, S100A4, S100A8/A9, and OPN, in any desired combination. According to certain embodiments, such a panel of probes includes probes for binding to 50 or fewer, 40 or fewer, 30 or fewer, 25 or fewer, 20 or fewer, 15 or fewer, 10 or fewer, 9 or fewer, 8 or fewer, 7 or fewer, 6 or fewer, 5 or fewer, 4 or fewer, 3, or 2 analytes.

According to certain embodiments, the sensor devices (e.g., magnetic sensor devices) of the present disclosure include a panel of probes that includes probes for specific binding to 2, 3, 4, 5 or each of TIMP1, anti-ANGPTL3, EGFR, ProSB, anti-YWHAQ, and anti-LAMR1. Such a panel may include one or more probes for specific binding to one or more additional unique circulating analytes (e.g., 20 or fewer additional analytes). The additional analytes may be selected from HE4, AGR2, CHGA, LRG1, anti-ANXA1, anti-UBQLN1, IL6, IL8, CXCL2, DEFB1, FGF2, CD97, PPBP, PCT, RAGE, S100A4, S100A8/A9, OPN, and any combination thereof. The panel of probes may include probes for binding to 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, or each of the additional analytes. Such a panel of probes may include probes for binding to 50 or fewer, 40 or fewer, 30 or fewer, 25 or fewer, 20 or fewer, 15 or fewer, 10 or fewer, 9 or fewer, 8 or fewer, 7 or fewer, 6 or fewer, 5 or fewer, 4 or fewer, or 3 analytes.

The panel of probes included in a sensor device of the present disclosure may further include probes for binding to circulating cells (such as circulating tumor cells (CTCs), circulating stem cells, and/or the like) and/or circulating nucleic acids (such as circulating DNA (e.g., circulating tumor DNA) and/or circulating RNA), as described hereinabove.

Magnetic Sensor Devices

According to certain embodiments, a sensor device of the present disclosure is a magnetic sensor device. Magnetic sensor devices of the present disclosure may include a magnetic sensor chip that includes a panel of probes (e.g., attached to a surface of the magnetic sensor chip), including any of the panels of the probes described elsewhere herein. In certain aspects, the magnetic sensor chip comprises two or more magnetic sensors having capture probes attached to the surface thereof (e.g., as an addressable capture probe array). Each of the two or more magnetic sensors having capture probes attached to the surface thereof may include capture probes for binding to the same 2 or more circulating analytes.

Aspects of magnetic sensor devices and systems will now be described.

Magnetic Sensors

In certain aspects, a magnetic sensor device of the present disclosure includes one or more magnetic sensors. In some cases, the one or more magnetic sensors are configured to detect the presence of nearby magnetic labels without any direct physical contact between the magnetic sensor and the magnetic label. In certain embodiments, the magnetic sensors are configured to detect the presence of analytes of the two or more circulating analytes that may be present in the blood sample. For example, a magnetic label may be bound, either directly or indirectly, to an analyte, which in turn may be bound, either directly or indirectly, to the magnetic sensor. If the bound magnetic label is positioned within the detection range of the magnetic sensor, then the magnetic sensor may provide a signal indicating the presence of the bound magnetic label, and thus indicating the presence of the analyte.

In some instances, the magnetic sensors have a detection range from 1 nm to 1000 nm from the surface of the magnetic sensor, such as from 1 nm to 800 nm, including from 1 nm to 500 nm, such as from 1 nm to 300 nm, including from 1 nm to 100 nm, or from 1 nm to 75 nm, or from 1 nm to 50 nm, or from 1 nm to 25 nm, or from 1 nm to 10 nm from the surface of the magnetic sensor. In some instances, a minimization of the detection range of the sensors may facilitate detection of specifically bound analytes while minimizing detectable signals from analytes not of interest. By "detection range" is meant the distance from the surface of the magnetic sensor where the presence of a magnetic label will induce a detectable signal in the magnetic sensor.

In some cases, magnetic labels positioned close enough to the surface of the magnetic sensor to be within the detection range of the magnetic sensor will induce a detectable signal in the magnetic sensor. In certain instances, magnetic labels positioned at a distance from the surface of the magnetic sensor that is greater than the detection range of the magnetic sensor will not induce a detectable or non-negligible signal in the magnetic sensor. For example, a magnetic label may have a magnetic flux that is proportional to $1/r^3$, where r is the distance between the magnetic sensor and the magnetic label. Thus, only those magnetic labels that are positioned in close proximity (e.g., within the detection range of the magnetic sensor) will induce a detectable signal in the magnetic sensor.

As noted, probes of the panel of probes may be bound to the surface of the magnetic sensor. For instance, a cationic polymer such as polyethyleneimine (PEI) can be used to nonspecifically bind charged probes (e.g., antibodies, antigens, ligands, nucleic acids, etc.) to the sensor surface via physiabsorption (physical absorption). Alternatively, a covalent chemistry can be used utilizing free amines or free thiol groups on the analyte-specific probe to covalently bind the analyte-specific probe to the surface of the magnetic sensor. For example, an N-hydroxysuccinimide (NHS) to 1-ethyl-3-(3-dimethylaminopropyl) carbodiimide (EDC) coupling system may be used to covalently bind the analyte-specific probe to the surface of the magnetic sensor.

In certain embodiments, the magnetic sensor is configured to generate an electrical signal in response to a magnetic label in proximity to a surface of the magnetic sensor. For example, the magnetic sensors may be configured to detect changes in the resistance of the magnetic sensor induced by changes in the local magnetic field. In some cases, binding of a magnetic label (e.g., a magnetic nanoparticle label) in close proximity to the magnetic sensor, as described above, induces a detectable change in the resistance of the magnetic sensor. For instance, in the presence of an applied external magnetic field, the magnetic labels near the magnetic sensor may be magnetized. The local magnetic field of the magnetized magnetic labels may induce a detectable change in the resistance of the underlying magnetic sensor. Thus, the presence of the magnetic labels can be detected by detecting changes in the resistance of the magnetic sensor. In certain embodiments, the magnetic sensors are configured to detect changes in resistance of 1 Ohm or less, such as 500 mOhm or less, including 100 mOhm or less, or 50 mOhm or less, or 25 mOhm or less, or 10 mOhm or less, or 5 mOhm or less, or 1 mOhm or less. In certain embodiments, the change in resistance may be expressed in parts per million (PPM) relative to the original sensor resistance, such as a change in resistance of 2 PPM or more, or 20 PPM or more, or 200 PPM or more, or 400 PPM or more, or 600 PPM or more, or 1000 PPM or more, or 2000 PPM or more, or 4000 PPM or more, or 6000 PPM or more, or 10,000 PPM or more, or 20,000 PPM or more, or 40,000 PPM or more, or 60,000 PPM or more, or 100,000 PPM or more, or 200,000 PPM or more.

The magnetic sensor may include a magnetoresistive element. Suitable magnetoresistive elements include, but are not limited to, spin valve magnetoresistive elements and magnetic tunnel junction (MTJ) magnetoresistive elements.

In certain embodiments, the magnetic sensor element is a spin valve magnetoresistive element. In certain cases, the spin valve element is a multilayer structure that includes a first ferromagnetic layer, a non-magnetic layer disposed on the first ferromagnetic layer, and a second ferromagnetic layer disposed on the non-magnetic layer. The first ferromagnetic layer may be configured to have its magnetization vector fixed in a certain direction. In some cases, the first ferromagnetic layer is called the "pinned layer". In certain embodiments, the spin valve element includes a pinned layer with a magnetization substantially parallel to a width of the magnetic sensor element. The second ferromagnetic layer may be configured such that its magnetization vector can rotate freely under an applied magnetic field. In some cases, the second ferromagnetic layer is called the "free layer". In some cases, the first ferromagnetic layer (which may be referred to as the "pinned layer"), is replaced by a synthetic or artificial antiferromagnet which consists of two antiparallel ferromagnetic layers separated by a nonmagnetic spacer: one of the ferromagnetic layers (which may be referred to as the "reference layer"), is underneath the non-magnetic layer which is under the "free layer"; the other ferromagnetic layer (the other "pinned layer"), is usually "pinned" by a natural antiferromagnet such as IrMn, PtMn, FeMn, or NiO.

In certain instances, the electrical resistance of a spin valve element depends on the relative orientation of the magnetization vector of the free layer to that of the pinned layer. When the two magnetization vectors are parallel, the resistance is the lowest; when the two magnetization vectors are antiparallel, the resistance is the highest. The relative change of resistance is called the magnetoresistance (MR) ratio. In certain embodiments, a spin valve element has a MR ratio of 1% to 20%, such as 3% to 15%, including 5% to 12%. In some cases, the MR ratio of a spin valve element is 10% or more in a small magnetic field, e.g., 100 Oe. Changes in the resistance of the spin valve element due to the presence of magnetic labels near the surface of the spin valve element may be detected, as described above.

In certain embodiments, the signal from the spin valve element due to the magnetic label depends on the distance between the magnetic label and the free layer of the spin valve element. In some cases, the voltage signal from a magnetic label decreases as the distance from the center of the magnetic label to the mid-plane of the free layer increases. Thus, in certain instances, the free layer in the spin valve element is positioned at the surface of the spin valve element. Positioning the free layer at the surface of the spin valve element may minimize the distance between the free layer and any bound magnetic labels, which may facilitate detection of the magnetic labels.

In certain embodiments, the spin valve element may include a passivation layer disposed on one or more of the spin valve element surfaces. In some cases, the passivation layer has a thickness of 60 nm or less, such as 50 nm or less, including 40 nm or less, 30 nm or less, 20 nm or less, 10 nm or less. For instance, the passivation layer may have a thickness of 1 nm to 10 nm, such as from 1 nm to 5 nm, including from 1 nm to 3 nm. In certain embodiments, the passivation layer includes gold, tantalum, $SiO_2$, $Si_3N_4$, combinations thereof, and the like.

In certain embodiments, the magnetic sensor element is a magnetic tunnel junction (MTJ) magnetoresistive element (also referred to herein as an MTJ element). In some cases, the MTJ element includes a multilayer structure that includes a first ferromagnetic layer, an insulating layer disposed on the first ferromagnetic layer, and a second ferromagnetic layer disposed on the insulating layer. The insulating layer may be a thin insulating tunnel barrier, and may include alumina, MgO, and the like. In some cases, electron tunneling between the first and the second ferromagnetic layers depends on the relative magnetization of the two ferromagnetic layers. For example, in certain embodiments, the tunneling current is high when the magnetization vectors of the first and second ferromagnetic layers are parallel and the tunneling current is low when the magnetization vectors of the first and second ferromagnetic layers antiparallel. In some cases, the first ferromagnetic layer may be replaced by a synthetic or artificial antiferromagnet which consists two antiparallel ferromagnetic layers separated by a nonmagnetic spacer: one of the ferromagnetic layers may be underneath the tunnel barrier; the other ferromagnetic layer may be "pinned" by a natural antiferromagnet such as IrMn, PtMn, or FeMn.

In some instances, a MTJ element has a magnetoresistance ratio (MR) of 1% to 300%, such as 10% to 250%, including 25% to 200%. Changes in the resistance of the MTJ element due to the presence of magnetic labels near the surface of the MTJ element may be detected, as described above. In some instances, the MTJ element has an MR of 50% or more, or 75% or more, or 100% or more, or 125% or more, or 150% or more, or 175% or more, or 200% or more, or 225% or more, or 250% or more, or 275% or more, or 200% or more. For instance, the MTJ element may have an MR of 225% or more.

In certain embodiments, the second ferromagnetic layer (e.g., the layer of the MTJ element positioned at the surface of the MTJ element) includes two of more layers. For example, the second ferromagnetic layer may include a first layer, a second layer disposed on the first layer, and a third layer disposed on the second layer. In some cases, the first layer is a thin ferromagnetic layer (e.g., NiFe, CoFe, CoFeB, and the like). The thin metallic layer may have a thickness of 6 nm or less, such as 5 nm or less, including 4 nm or less, 3 nm or less, 2 nm or less, or 1 nm or less, or 0.5 nm or less. The second layer may include a conductive metal, e.g., copper, aluminum, palladium, a palladium alloy, a palladium oxide, platinum, a platinum alloy, a platinum oxide, ruthenium, a ruthenium alloy, a ruthenium oxide, silver, a silver alloy, a silver oxide, tin, a tin alloy, a tin oxide, titanium, a titanium alloy, a titanium oxide, tantalum, a tantalum alloy, a tantalum oxide, combinations thereof, and the like. The second layer may have a thickness of 2 nm or less, such as 0.5 nm or less, including 0.4 nm or less, 0.3 nm or less, 0.2 nm or less, or 0.1 nm or less. The third layer may include a ferromagnetic material such as, but not limited to, NiFe, CoFe, CoFeB, and the like. The third layer may have a thickness of 6 nm or less, such as 5 nm or less, including 4 nm or less, 3 nm or less, 2 nm or less, or 1 nm or less, or 0.5 nm or less.

In some cases, the MTJ element is configured such that the distance between an associated magnetic label and the top surface of the free layer ranges from 5 nm to 1000 nm, or 10 nm to 800 nm, such as from 20 nm to 600 nm, including from 40 nm to 400 nm, such as from 60 nm to 300 nm, including from 80 nm to 250 nm.

The MTJ element may include a passivation layer disposed on one or more of the MTJ element surfaces. In some instances, the passivation layer has a thickness of 60 nm or less, such as 50 nm or less, including 40 nm or less, 30 nm or less, 20 nm or less, 10 nm or less. For example, the passivation layer may have a thickness of 1 nm to 50 nm, such as from 1 nm to 40 nm, including from 1 nm to 30 nm, or form 1 nm to 20 nm. In some instances, the passivation layer has a thickness of 30 nm. In some cases, the passivation layer includes gold, tantalum, a tantalum alloy, a tantalum oxide, aluminum, an aluminum alloy, an aluminum oxide, $SiO_2$, $Si_3N_4$, $ZrO_2$, combinations thereof, and the like. In certain embodiments, a passivation layer with a thickness as described above facilitates a maximization in signal detected from magnetic labels specifically bound to the sensor surface while minimizing the signal from magnetic labels that are not specifically bound.

In certain embodiments, a MTJ element has dimensions ranging from 1 µm×1 µm to 200 µm×200 µm, including dimensions of 1 µm×200 µm or less, such as 200 µm×1 µm or less, for instance 150 µm×10 µm or less, or 120 µm×5 µm or less, or 120 µm×0.8 µm or less, or 0.8 µm×120 µm or less, or 100 µm×0.7 µm or less, or 100 µm×0.6 µm or less, or 100 µm×0.5 µm or less, or 10 µm×0.6 µm or less, or 10 µm×0.5 µm or less. In some instances, a MTJ element has dimensions of 120 µm×0.8 µm or less, such as 2.0 µm×0.8 µm.

Magnetic tunnel junction (MTJ) detectors are further described in U.S. Application Publication No. 2009/0104707, filed Sep. 19, 2008, the disclosure of which is hereby incorporated by reference in its entirety. Detectors are further described in U.S. Pat. No. 7,906,345, filed Apr. 22, 2004, the disclosure of which is hereby incorporated by reference in its entirety.

In certain cases, the magnetic sensor is a multilayer thin film structure. A sensor may include alternating layers of a ferromagnetic material and a non-magnetic material. The ferromagnetic material may include, but is not limited to, Permalloy (NiFe), iron cobalt (FeCo), nickel iron cobalt (NiFeCo), CoFeB, combinations thereof, and the like. In some cases, the non-magnetic material is an noble metal, such as, but not limited to, Cu, Au, Ag, and the like. In certain embodiments, the ferromagnetic layers have a thickness of 1 nm to 10 nm, such as 2 nm to 8 nm, including 3 nm to 4 nm. In some instances, the non-magnetic layer has a thickness of 0.2 nm to 5 nm, such as 1 nm to 3 nm, including 1.5 nm to 2.5 nm, or 1.8 nm to 2.2 nm.

In certain embodiments, the magnetic sensor device may be configured to include one or more magnetic sensing areas. A magnetic sensing area may correspond to the area of the device where an array of magnetic sensors (e.g., an array of biosensors) is positioned. For instance, the magnetic sensing area may be an area on the surface of the device that is exposed to the blood sample during use, and which has an array of magnetic sensors as described above.

The magnetic sensing area may be configured to include a fluid reservoir. The fluid reservoir may be any of a variety of configurations, where the fluid reservoir is configured to hold a blood sample in contact with the magnetic sensor arrays. Accordingly, configurations of the fluid reservoirs may include, but are not limited to: cylindrical well configurations, square well configurations, rectangular well configurations, round bottom well configurations, and the like. For instance, the fluid reservoirs may include walls that separate one fluid reservoir from adjacent fluid reservoirs. The walls may be substantially vertical with respect to the surface of the reservoir plate. In some cases, the walls of each fluid reservoir define a volume of space that may receive a volume of sample equal to or less than the volume of space defined by the fluid reservoir.

In certain embodiments, a fluid reservoir has a volume of 10 mL or less, or 5 mL or less, or 3 mL or less, or 1 mL or less, such as 500 µL or less, including 100 µL or less, for example 50 µL or less, or 25 µL or less, or 10 µL or less, which is sufficient to contain a sample volume of an equal or lesser volume.

Magnetic Sensor Systems

Aspects of the present disclosure include magnetic sensor systems. In some embodiments, the magnetic sensor system includes a magnetic sensor device, and a magnetic field source. The magnetic sensor device includes a support having one or more arrays of magnetic sensors (e.g., arrays of biosensors) positioned thereon. The system may be configured to obtain signals from the one or more arrays of magnetic sensors indicating whether analytes of the two or more circulating analytes are present in one or more corresponding blood samples.

In certain embodiments, the system includes a magnetic field source. The magnetic field source may be configured to apply a magnetic field to the magnetic sensor device (e.g., the magnetic sensor arrays) sufficient to produce a DC and/or AC field in the assay sensing area (e.g. in the area where the magnetic sensor arrays are positioned during signal acquisition). In some instances, the magnetic field source is configured to produce a magnetic field with a magnetic field strength of 1 Oe or more, or 5 Oe or more, or 10 Oe or more, or 20 Oe or more, or 30 Oe or more, or 40 Oe or more, or 50 Oe or more, or 60 Oe or more, or 70 Oe or more, or 80 Oe or more, or 90 Oe or more, or 100 Oe or more.

The magnetic field source may be positioned such that a magnetic field is produced in the area where the magnetic sensor arrays are positioned when the magnetic sensor device is in use. In some cases, the magnetic field source is configured to generate a uniform, controllable magnetic field around the set of fluid reservoirs on the reservoir plate where an assay is being performed. The magnetic field source may include one or more, such as two or more, three or more, four or more magnetic field generating components. In some cases, the magnetic field source may include one or more electromagnets, such as coil electromagnets. The coil electromagnets may include wire-wound coils. For example, the magnetic field source may include two electromagnets arranged in a Helmholtz coil geometry.

Embodiments of the systems further include computer-based systems. The systems may be configured to qualitatively and/or quantitatively assess binding interactions as described above. A "computer-based system" refers to the hardware, software, and data storage components used to analyze the signals from the magnetic sensors. The hardware of the computer-based systems may include a central processing unit (CPU), inputs, outputs, and data storage components. Any of a variety of computer-based systems is suitable for use in the subject systems. The data storage components may include any computer readable medium for recording signals from the magnetic sensor arrays, or an accessible memory component that can store signals from the magnetic sensor arrays.

To "record" data, programming or other information on a computer readable medium refers to a process for storing information, using any such methods as known in the art. Any convenient data storage structure may be chosen, depending on the method used to access the stored information. A variety of data processor programs and formats can be used for storage, e.g. word processing text file, database format, etc.

In certain embodiments, the system includes an activation and signal processing unit. The activation and signal processing unit may be configured to operably couple to the magnetic sensor device. In some instances, the activation and signal processing unit is electrically coupled to the magnetic sensor device. The activation and signal processing unit may be electrically coupled such as to provide bi-directional communication to and from the magnetic sensor device. For example, the activation and signal processing unit may be configured to provide power, activation signals, etc. to components of the magnetic sensor device, such as, but not limited to the magnetic sensor arrays. As such, the activation and signal processing unit may include an activation signal generator. The activation signal generator may be configured to provide power, activation signals, etc. to components of the analyte detection device, such as, but not limited to the magnetic sensor arrays. In some instances, the activation and signal processing unit is configured to apply a voltage across the magnetic sensor arrays ranging from 1 mV to 10 V, such as 100 mV to 5 V, including 200 mV to 1 V, for example, 300 mV to 500 mV. In some cases, the activation and signal processing unit is configured to apply a voltage across the magnetic sensor arrays of 500 mV.

Additionally, the activation and signal processing unit may be configured to receive signals from the magnetic sensor device, such as from the magnetic sensor arrays of the magnetic sensor device. The signals from the magnetic sensor(s) of the magnetic sensor device may be used to detect the presence of analytes of the two or more circulating analytes in the blood sample(s). In some instances, the activation and signal processing unit may include a processor configured to output an analyte detection result in response to receiving signals from the magnetic sensor arrays. Thus, the processor of the activation and signal processing unit may be configured to receive signals from the magnetic sensor device, process the signals according to a predetermined algorithm, obtain a result related to the presence of one or more analytes in the samples, and output the result to a user in a human-readable or an audible format.

Models which may be used, e.g., to diagnose the subject as having cancer (e.g., lung cancer, such as non-small cell lung cancer) include those described herein in the Examples section and FIGS. 8 and 9.

A "processor" references any hardware and/or software combination that will perform one or more programmed functions. For example, any processor herein may be a programmable digital microprocessor such as available in the form of an electronic controller, mainframe, server or personal computer (e.g., desktop or portable). Where the processor is programmable, suitable programming can be communicated from a remote location to the processor, or previously saved in a computer program product (such as a portable or fixed computer readable storage medium, whether magnetic, optical or solid-state device based). For example, a magnetic medium, optical disk or solid-state memory device may carry the programming, and can be read by a suitable reader communicating with the processor.

In some instances, the subject systems are configured to modulate the current applied to the magnetic sensor arrays (e.g., the sense current). The subject systems may also be configured to modulate the magnetic field generated by the magnetic field source. Modulating the sense current and the magnetic field may facilitate a minimization in signal noise, and thus a maximization in the signal to noise ratio. Additional aspects of modulating the sense current and the magnetic field are described in more detail in U.S. application Ser. No. 12/759,584, entitled "Methods and Devices for Detecting the Presence of an Analyte in a Sample, filed on Apr. 13, 2010, the disclosure of which is incorporated herein by reference in its entirety.

Embodiments of the subject systems may also include the following components: (a) a wired or wireless communications module configured to transfer information between the system and one or more users, e.g., via a user computer, as described below; and (b) a processor for performing one or more tasks involved in the qualitative and/or quantitative analysis of the signals from the magnetic sensors. In certain embodiments, a computer program product is provided that includes a computer-usable medium having control logic (e.g., a computer software program, including program code) stored therein. The control logic, when executed by the processor of the computer, causes the processor to perform functions described herein. In other embodiments, some functions are implemented primarily in hardware using, for example, a hardware state machine. Implementation of the hardware state machine so as to perform the functions described herein may be accomplished using any convenient method and techniques.

In addition to the magnetic sensor device and activation and signal processing unit, the systems may include a number of additional components, such as, but not limited to: data output devices, e.g., monitors, speakers, etc.; data input devices, e.g., interface ports, buttons, switches, keyboards, etc.; fluid handling components, e.g., microfluidic components; power sources; power amplifiers; wired or wireless communication components; etc. For example, the systems may include fluid handling components, such as microfluidic fluid handling components. In certain embodiments, the microfluidic fluid handling components are configured to deliver a fluid to the fluid reservoirs of the reservoir plate. In some cases, the fluid includes one or more of the following: an assay composition, a blood sample, one or more detection reagents (e.g., detection antibodies, magnetic labels, and/or the like). In certain instances, the microfluidic fluid handling components are configured to deliver small volumes of fluid, such as 1 mL or less, such as 500 µL or less, including 100 µL or less, for example 50 µL or less, or 25 µL or less, or 10 µL or less.

In certain embodiments, the system is a high-sensitivity analyte detector. By "high-sensitivity" is meant that the system is configured to detect an analyte in a sample, where the concentration of the analyte in the sample is low. In some cases, the system is configured to produce a detectable signal indicating the presence of an analyte of interest in a sample where the concentration of the analyte in the sample is 1 µM or less, such as 100 nM or less, or 10 nM or less, or 1 nM or less, including 100 pM or less, or 10 pM or less, or 1 pM or less, for example 500 fM or less, or 250 fM or less, or 100 fM or less, or 50 fM or less, or 25 fM or less, such as 10 fM or less, or 5 fM or less, or 1 fM or less. Stated another way, the system may be configured to have a detection limit, e.g., a lower limit of quantitation (LLOQ), of 1 µM or less, such as 100 nM or less, or 10 nM or less, or 1 nM or less, including 100 pM or less, or 10 pM or less, or 1 pM or less, for example 500 fM or less, or 250 fM or less, or 100 fM or less, or 50 fM or less, or 25 fM or less, such as 10 fM or less, or 5 fM or less, or 1 fM or less.

In certain embodiments, the systems include a display. The display may be configured to provide a visual indication of an analyte detection result obtained from the activation and signal processing unit, as described above. The display may be configured to display a qualitative analyte detection result. For instance, the qualitative display may be configured to display qualitative indicators to a user that a sample includes or does not include a specific analyte of interest. In some embodiments, the display may be configured to display an analyte detection result, where the analyte detection result is a quantitative result, e.g., a quantitative measurement of the concentration of an analyte in a sample. For example, in embodiments where the system is configured to output a quantitative analyte detection result, the system may include a display configured to display the quantitative analyte detection result.

The magnetic sensor device optionally includes a programmable memory, which prior to and during the use of the magnetic sensor device can be programmed with relevant information such as: calibration data for each individual sensor; a record of how the biochip has been prepared with surface functionalization molecules prior to the assay; a record of all completed assay steps; a record about which sample was measured; a record of the measurement results; and the like.

Additional aspects of magnetic sensor systems are described in more detail in U.S. Pat. Nos. 9,151,763 and 9,164,100, and U.S. Application Publication No. 2015/0377893, the disclosures of each of which are incorporated herein by reference.

Exemplary Embodiments

Aspects of the present disclosure include a magneto-nanosensor technology for blood-based diagnosis and management of NSCLC. Current protein technologies advanced to the clinic are ELISA-based or rely on expensive mass spectrometry (MS) methods. Magneto-nanosensors overcome detection limitations of ELISA-based chemistry and the high cost and slow throughput of MS technologies. Furthermore, magneto-nanosensors are capable of multiplexing up to 80 individual detectors at one time for high-throughput read out of biomarkers on an instrument configured to read tens of patient samples simultaneously. A blood test described herein was developed to identify patients with lung cancer using highly sensitive, inexpensive, and high throughput magneto-nanosensors to measure a protein panel including two or more biomarkers. Given the increase in lung cancer screening and incidentally detected lung nodules discovered during medical imaging, the methods and devices described herein will provide critical data to fill the gap in a clinician's information and serve a critical need in lung cancer care.

Aspects of the present disclosure also include the integration of the magneto-nanosensor technology as an adjuvant blood test with clinical imaging and clinical parameters to detect NSCLC. Models to predict lung cancer have relied for over 15 years on imprecise demographic data like age and smoking history as well as nodule characteristics from computed tomography images. While useful, such models are overly simplistic and accurate only 70 to 80% of the time. The inventors have developed a multivariate model using imaging and clinical parameters along with circulating analytes measured with magneto-nanosensor technology, to improve lung cancer prediction in its early stages. The model has clinical utility for the large population of patients undergoing lung cancer evaluation as either a stand-alone assessment, or in conjunction with standard clinical assessments and other cancer biomarkers. The model can also be adapted for screening high-risk populations for lung cancer and for therapy prediction and monitoring of lung cancer patients after diagnosis.

The ability to quantify lower concentrations (fM or pg/mL levels) of circulating proteins and autoantibodies with good precision and reproducibility enables detection of early-stage cancers and is a requirement for next-generation diagnostics. The magneto-nanosensor immunoassay platform from MagArray, Inc. meets such requirements and is capable of detecting up to 80 distinct circulating analytes in a multiplex format. The test is well suited for applications where measuring multiple circulating analytes simultaneously with high sensitivity and specificity may be needed for complex diseases such as early-stage NSCLC.

The principles of the MagArray magneto-nanosensor chips incorporating giant magnetoresistive (GMR) sensors are shown in FIG. 1. The GMR sensor surfaces are coated with immobilized antigens or antibodies to capture analytes (autoantibodies or antigens) in a sandwich-type immunoassay format. Biotinylated detection antibodies form the second half of the immunoassay and allow streptavidin-conjugated magnetic nanoparticles (50-nm, MNPs) to bind and perturb the local magnetic fields and alter the sensor resistances. The MNPs are therefore detected in real time by monitoring the resistance changes in the GMR sensor. The sensor resistance signal (expressed as parts per million, ppm) is correlated to the analyte concentration (in pg/mL or femtomoles/L, fM). The magneto-nanosensors may be used to detect plasma biomarkers, such as CEA, as low as 5 femtomolar (or 1 pg/mL) with a dynamic range of ~4-6 logs, and allow multiplexing of blood biomarkers with negligible cross-reactivity. Antigen-based capture for the sensitive detection of autoantibodies has also been demonstrated.

Figure 2:
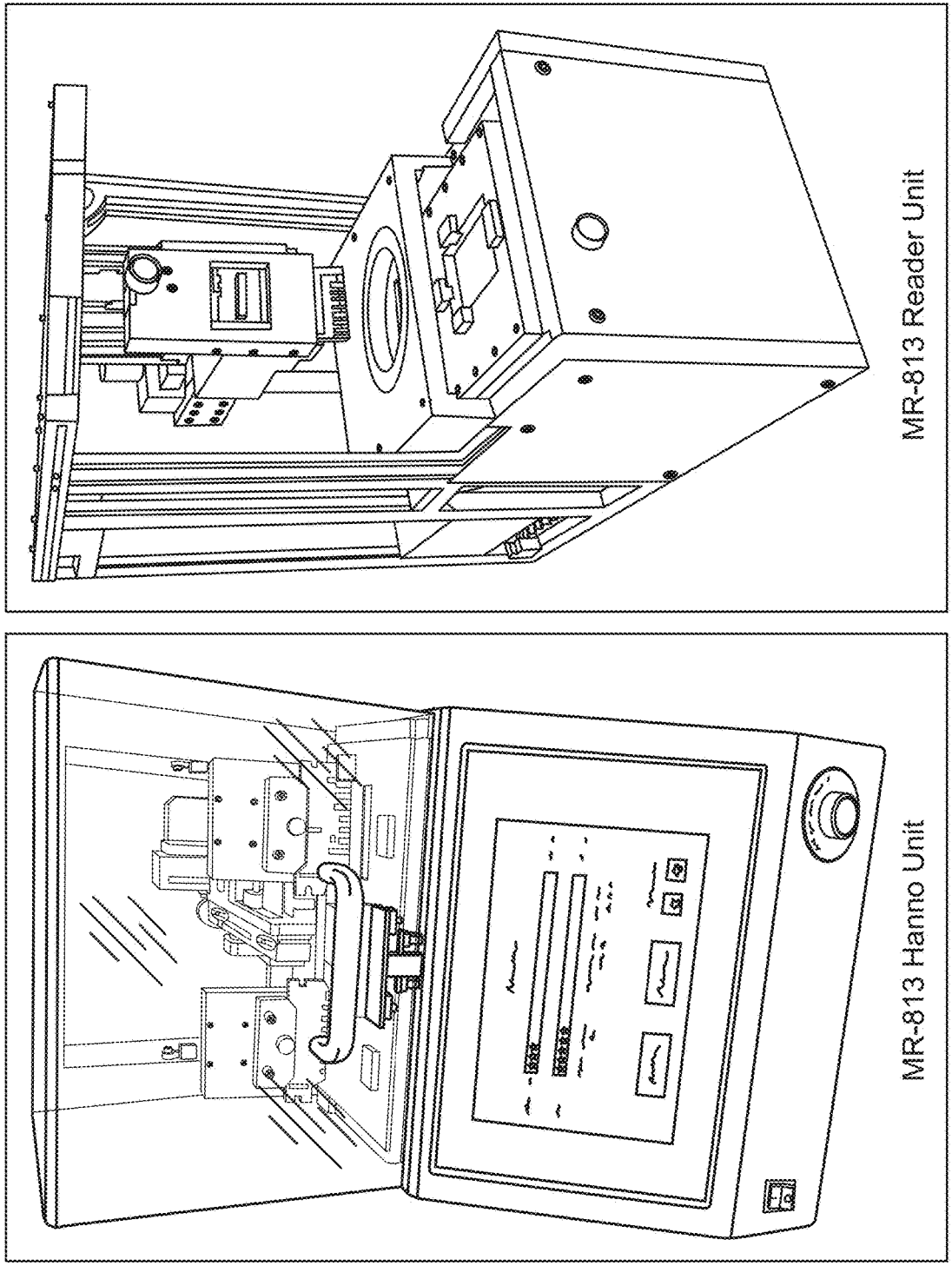
FIG. 2 shows images of a modular biochemistry mixing station (MR-813 Hanno Unit) and a reader station (MR-813 Reader Unit) for simultaneous analysis of 8- or 16-sample batches, according to embodiments of the present disclosure.

A MagArray instrument system ("MR-813"), shown in FIG. 2, is capable of assaying 16 or more samples simultaneously. MR-813 represents a second-generation device compared to another MagArray instrument ("MC-113") which was designed for single-sample processing only.

Figure 3:
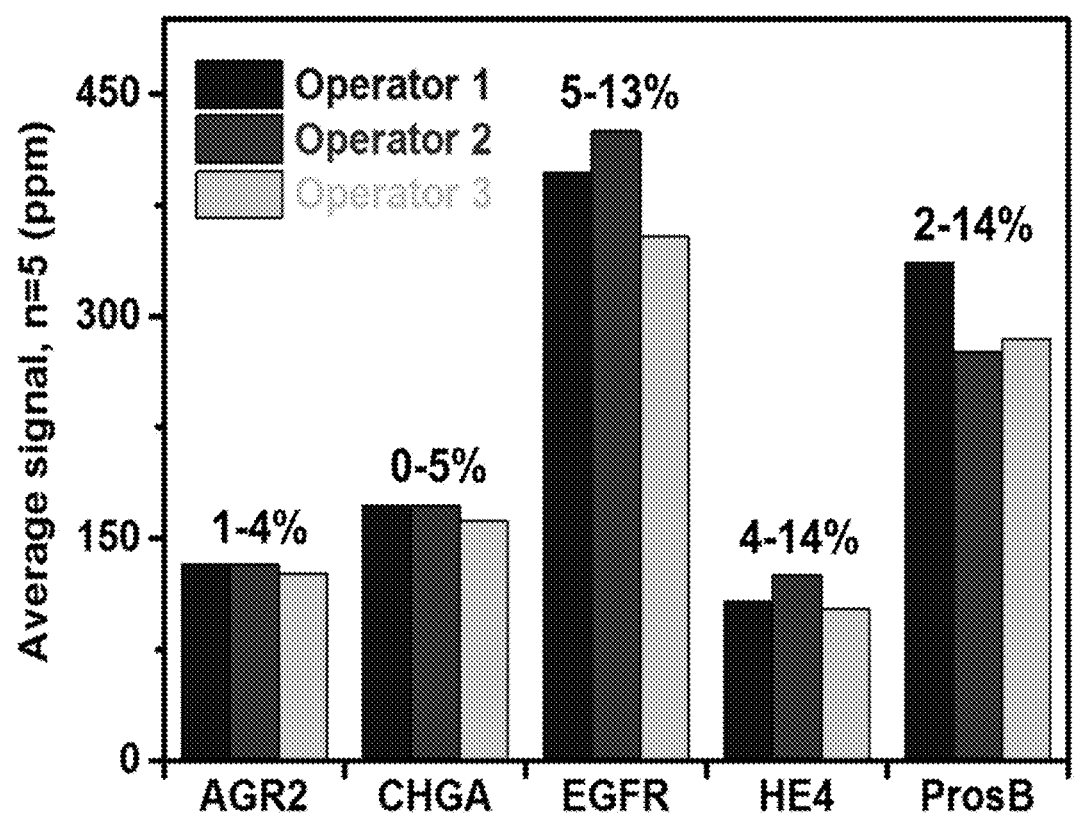
FIG. 3 shows a graph of Coefficients of Variation (CV). A 5-plex protein biomarker assay was reproducibility performed by three different operators. Each operator repeatedly (n=5) measured the biomarkers using multiplexed magneto-nanosensor chips. The range of inter-assay CVs obtained by all operators is indicated for each marker.

An important feature of magneto-nanosensors is low inter-assay CV, which is generally <15% for all analytes at physiological concentrations of interest. FIG. 3 illustrates CVs ranging from 0 to 14% for five circulating antigens for NSCLC diagnosis: AGR2, CHGA, EGFR, HE4, and pro-SFTPB.

Early-stage NSCLC is unlikely to produce large quantities of circulating analytes for detection. The MagArray technology is capable of detecting multiple protein biomarkers at femtomolar levels, far surpassing current commercial methods. Sensitive and multiplexed detection of circulating proteins and autoantibodies with high target specificity will allow the accurate detection of NSCLC earlier, both alone and in combination with clinical parameters and imaging methods. To this end, a circulating protein and autoantibody panel was tested on the MR-813 instrument in a training cohort of 201 patients, according to rigorous analyte study design principles. The cohort consisted of patients who ultimately had a benign or malignant diagnosis (NSCLC or other non-NSCLC malignancies, such as metastasis from other areas of the body). There were 82 patients with stage I NSCLC, 36 with stage II-IV cancer, by pathologic diagnosis, and 83 with lung lesions that were not cancer. A benign diagnosis is defined by two-year nodule stability, nodule resolution, or the clinical diagnosis of an alternative non-malignant diagnosis based on culture or biopsy data. Those patients lost to follow-up or who remained with an uncertain diagnosis per the medical chart, or who had a non-NSCLC malignancy of the thorax, were also excluded. Patients assigned to a diagnostic group underwent required clinical and imaging data for analysis. Plasma obtained at the time of the subject's entry into the study were stored at −80° C., until all samples could be processed at once to avoid batch effects. The samples were run in multiplexed protein and autoantibody assay panels on the MagArray system by technicians who were blinded to the clinical diagnosis of the subjects. The protein assay panel measured Epidermal Growth Factor Receptor (EGFR), Human Epididymis Protein 4 (HE4), Pro-surfactant Protein B (pro-SFTPB; also referred to herein as "pro-SB"), Anterior Gradient Protein 2 (AGR2), Chromogranin A (CHGA), Leucine-rich Alpha-2-glycoprotein 1 (LRG1), and Tissue Inhibitor of Metalloproteinases 1 (TIMP1). The second multiplexed assay panel measured plasma autoantibodies against ANXA1 (Annexin 1), Laminin Alpha 1 (LAMR1), 14-3-3 Protein theta (a.k.a. YWHAQ), and Angiopoietin-like Protein 3 (ANGPTL3), and Ubiquilin 1 (UBQLN1). Circulating proteins and autoantibodies have shown promise for early diagnosis in NSCLC. For example, TIMP-1 is a broadly inducible endogenous inhibitor of metalloproteinases in the lung with cell proliferative and anti-apoptotic effects. It is associated with cancer in multiple disease sites including skin and lung cancer. TIMP-1 is a putative lung cancer diagnostic biomarker in blood because it is a secreted protein. Autoantibody against UBQLN1 in blood is a diagnostic marker for lung cancer (Chinnaiyan et al., U.S. Pat. No. 7,597,890).

In addition to circulating proteins, many genomic biomarkers may be used for lung cancer diagnostics. However, only a fraction of genomic biomarkers may lead to circulating proteins in blood. The inventors identified a list of circulating proteins that are either related to the gene biomarkers for lung cancer or associated with inflammation as reported in the literature. These proteins can be incorporated with the protein biomarkers disclosed earlier to further enhance the accuracy for early detection of lung cancers since the expression of protein biomarkers may provide more reliable clinical information for early development of lung cancer than genomic information alone. The additional proteins include: IL6 (interleukin 6); IL8 (interleukin 8); CXCL2 (chemokine (C-X-C motif) ligand 2); DEFB1 (defensin, beta 1); FGF2 (fibroblast growth factor 2); CD97 (cluster of differentiation 97); PPBP (pro-platelet basic protein, aka chemokine (C-X-C motif) ligand 7 or CXCL7); PCT (procalcitonin); RAGE (receptor for advanced glycation endproducts); S100A4 (S100 calcium-binding protein A4); S100A8/A9 (S100 calcium-binding protein A8/A9 complex); OPN (osteopontin, aka bone sialoprotein I (BSP-1 or BNSP), early T-lymphocyte activation (ETA-1), secreted phosphoprotein 1 (SPP1), 2ar and Rickettsia resistance (Ric)).

The assays disclosed herein can be applied to subjects with pulmonary or other diseases to discern if they have lung cancer or not. The assays are also applicable to screening a population who are asymptomatic but have a high risk of lung cancer. For example, the latter includes persons who are 55 to 74 years of age with a minimum smoking history of 30 pack-years or more (pack-years=number of cigarette packs smoked per day×the number of years smoked) who currently smoke or have quit in the past 15 years and are disease-free at the time of screening.

Circulating analyte tests in isolation are less meaningful in the clinic where patient phenotype plays a large role in decision-making. Therefore, several pre-specified analyses were performed on the results of the plasma protein and autoantibody assays. First, the diagnostic accuracy of the panel alone to differentiate malignant from benign disease was determined, using a logistic regression model to generate sensitivity, specificity, NPV, and PPV metrics. Second, ascertained was the added value of the biomarker panels to traditional clinical measures of cancer risk in a model with more variables. Clinical and imaging variables included established markers of risk, including age, smoking history, cancer history, lung lesion size maximum diameter, lung lesion location (upper/lower lung), and $SUV_{max}$ intensity of the primary lesion. $SUV_{max}$ is the maximum standard uptake value of glucose metabolism by the lesion of interest. $SUV_{max}$ has been shown to correlate with a lesion's proliferative activity and is useful for cancer diagnosis in general and patient prognosis specifically in lung cancer. A significant result is defined as an increase in the model accuracy to predict cancer vs. benign cases at $p<0.05$ using logistic regression. Bootstrapping techniques were used to ensure the stability of the results and reduce the false discovery rate to develop a cancer risk score from the coefficients of the logistic regression model.

Utility

The subject methods and systems find use in a variety of different applications where determination of the presence or absence, and/or quantification of one or more analytes (e.g., circulating analytes) in a sample (e.g., a blood sample) is desired. The subject systems and methods also find use in applications where the screening of a plurality of samples is desired. In certain embodiments, the methods are directed to detection of a set of analytes, e.g., two or more distinct circulating analytes, in one or more samples. For example, the methods may be used in the rapid detection of two or more circulating analytes in a group of whole blood, plasma, or serum samples, e.g., as may be employed in the diagnosis of a disease condition (e.g., cancer, such as non-small cell lung cancer) in a subject, in the ongoing management or treatment of a disease condition in a subject, etc.

In certain embodiments, the subject methods and systems find use in detecting the presence or absence of particular circulating analytes, as well as an increase or decrease in the concentration of particular analytes in whole blood, plasma, serum, or other bodily fluids.

The presence or absence of particular circulating analytes or significant changes in the concentration of particular circulating analytes can be used to diagnose disease risk, presence of disease in a subject, or to tailor treatments for the disease in an individual. For example, the presence, absence, and/or concentrations of particular circulating analytes may influence the choices of drug treatment or administration regimes given to an individual. In evaluating potential drug therapies, the circulating analytes may be used as a surrogate for a natural endpoint such as survival or irreversible morbidity. If a treatment alters the circulating analytes, which has a direct connection to improved health, the circulating analytes can serve as a surrogate endpoint for evaluating the clinical benefit of a particular treatment or administration regime. Thus, personalized diagnosis and treatment based on the circulating analyte profile in a subject are facilitated by the subject methods and systems. Furthermore, the early detection of circulating analytes associated with diseases is facilitated by the picomolar and/or femtomolar sensitivity of the subject methods and systems (e.g., magnetic sensor-based methods and systems). Due to the capability of detecting a plurality of circulating analytes on a single sensor device (e.g., magnetic sensor device), the presently disclosed assay systems and methods finds use in screening of a plurality of samples in multiplexed molecular diagnostics.

In certain embodiments, the subject systems and methods find use in detecting circulating analytes for a disease or disease state. In some cases, the disease is a cellular proliferative disease, such as but not limited to, a cancer, a tumor, a papilloma, a sarcoma, or a carcinoma, and the like. Thus, the subject systems and methods find use in detecting the presence of a disease, such as a cellular proliferative disease, such as a cancer, tumor, papilloma, sarcoma, carcinoma, or the like.

Kits

Also provided are kits for practicing one or more embodiments of the above-described methods. The subject kits may vary, and may include various devices (e.g., any of the sensor devices (e.g., magnetic sensor devises) of the present disclosure) and reagents. Reagents and devices include those mentioned herein with respect to magnetic sensor devices or components thereof (such as a magnetic sensor array), magnetic labels, one or more panels of probes, detection reagents, buffers, etc. The reagents may be provided in separate containers, such that the reagents, magnetic labels, probes, etc. may be used individually as desired. Alternatively, one or more reagents, magnetic labels, probes, etc. may be provided in the same container such that the one or more reagents, magnetic labels, capture probes, etc. is provided to a user pre-combined.

In certain embodiments, the kits include a magnetic sensor device as described above, and a magnetic label. For example, the magnetic label may be a magnetic nanoparticle, as described above. In some instances, the kits include at least reagents finding use in the methods (e.g., as described above); and a computer readable medium having a computer program stored thereon, wherein the computer program, when loaded into a computer, operates the computer to qualitatively and/or quantitatively determine binding interactions of interest from a signal (e.g., a real-time signal) obtained from a sensor (e.g., a magnetic sensor); and a physical substrate having an address from which to obtain the computer program.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., CD, DVD, Bluray, computer readable memory device (e.g., a flash memory drive), etc., on which the information has been recorded. Yet another means that may be present is a website address which may be used via the Internet to access the information at a removed site. Any convenient means may be present in the kits.

As can be appreciated from the disclosure provided above, the present disclosure has a wide variety of applications. Accordingly, the following examples are offered for illustration purposes and are not intended to be construed as a limitation on the invention in any way. Those of skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

EXAMPLES

Example 1

Detection of Lung Cancer with a Clinical Model Plus Two Protein Biomarkers

Examined were patients who underwent a PET-CT scan for the diagnosis of a lung lesion or for cancer staging from an observational study of lung cancer across three medical centers. Magneto-nanosensors and sandwich immunoassays developed at Stanford University and MagArray, Inc. were used to measure TIMP-1 and autoantibodies to ANGPTL3 in the plasma of patients with lung cancer and non-cancer controls. The levels of the biomarkers in cohorts of those patients stratified by diagnosis and smoking status were then analyzed to understand the relationship of the biomarkers to diagnosis and to the patient's smoking status using ANOVA and logistic regression analysis.

The "MR-813" system, shown in FIG. 2, capable of assaying 8, 16 or more GMR sensor chips simultaneously, was used to assay the blood samples. Each GMR chip was incubated with either a patient sample, a control sample, or a standard sample. The modular biochemistry mixing station (MR-813 Hanno Unit) was used to perform incubation of the samples or controls or standards with the GMR chips, incubation of detection reagents, and washing steps in between as needed. The reader station (MR-813 Reader Unit) was used for simultaneous analysis of 8, 16 or more GMR chips by performing incubation of magnetic nanoparticle solutions with the GMR chips transferred from the Hanno Unit and interrogating sensor signals under a tickling magnetic field in real time.

Figure 4:
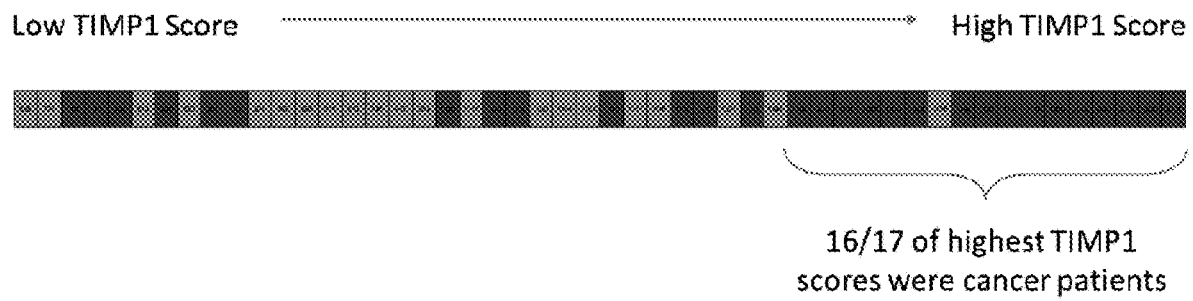
FIG. 4 shows a schematic showing that TIMP1 score is a good marker for predicting NSCLC in smokers, according to embodiments of the present disclosure.

20 µL of plasma from 201 patients was assayed—82 patients with stage I NSCLC, 36 with stage II-IV cancer, and 83 with lung lesions that were not cancer (benign controls). One hundred of these patients were past smokers, 50 were current smokers, and 51 were non-smokers. Past smoking was defined as not smoking at the time of enrollment. The average level of TIMP-1 was 102±5 ng/mL for all 201 patients. TIMP-1 levels were significantly different for all cancer cases vs. controls (p=0.03) but not for the stage I subgroup, or by matched analysis on age and lesion diameter. Stratified by smoking status, however, increasing TIMP-1 levels were associated with a cancer diagnosis for all stages (p=0.001), stage I only (p=0.005) and matched by age and lesion diameter (p=0.03), as shown in FIG. 4.

Figure 5:
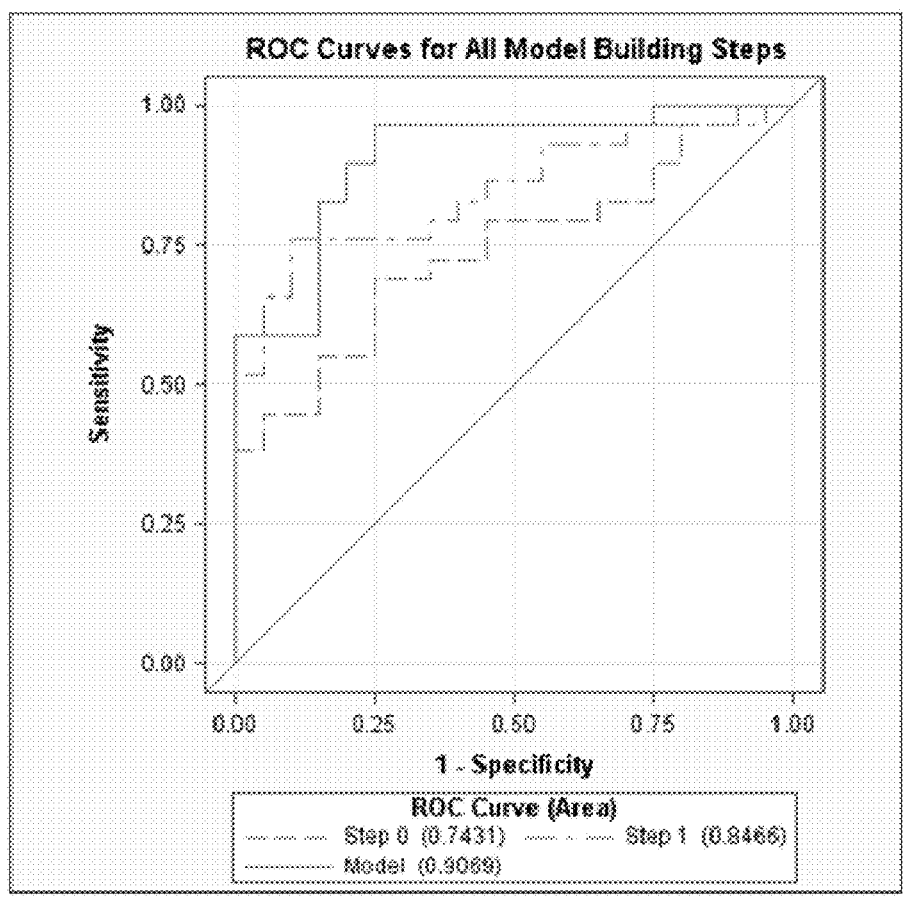
FIG. 5 shows a graph of Receiver Operator Characteristics (ROC) curves of the Clinical Model, the Clinical Model plus one protein marker, and the Clinical Model plus two protein markers, according to embodiments of the present disclosure.

Using clinically relevant data including age, cancer history, nodule diameter (cm), nodule lung location, and nodule border, NSCLC patients were capable of being distinguished from benign controls with an AUC of 0.741 (see "step 0" ROC curve in FIG. 5, which corresponds to the so called Clinical Model without the benefit of any protein biomarkers). Adding TIMP-1 protein data to the Clinical Model (see "step 1" ROC curve) improved the AUC to 0.8466. Adding another protein biomarker (antibody to ANGPTL3) to the logistic regression model gave an AUC of 0.9069 (see "Model" ROC in FIG. 5).

Example 2

Detection of Lung Cancer with Logistic Regression Models Incorporating Many Protein Biomarkers The eleven biomarker levels were transformed using the natural logarithm prior to logistic regression analyses. We evaluated the discriminatory ability of 28 predefined prediction models. These models were constructed by fitting logistic regression models according to the specifications in Table 1, with x denoting parameters included in a given model. The coefficients resulting from the model fit were used to construct a predictive model that was then evaluated using 1000 bootstrapped data sets. The ultimate measure of performance was the average ROC curve AUC determined for each model when applied to each bootstrapped data set.

Models 11-16 were constructed by first using a smoking score variable constructed as models 10, 9 and 8 consisting of biomarkers P3 and P6 with and without age and/or sex. These biomarkers were selected because they produced the best fitting model for predicting smoking status.

Model 25 was added to allow for a comparison between the performance of the best-performing smoking score model (Model 14) and a model using the same variables without a smoking score (Model 25). Model 25 contains the same variables as model 14, but uses all variables independently rather than combining some variables into a smoking score.

Twelve models produced AUC distributions with mean AUC greater than or equal to 0.8 (Table 1 in FIG. 8). The model selected via the previously applied lasso approach, Model 1, performed better than all other models. The next best performing model was model 17, which included age, sex, cancer diagnosis history, nodule location and P3, P6, P7, A1, A2, and A4.

Figure 6:
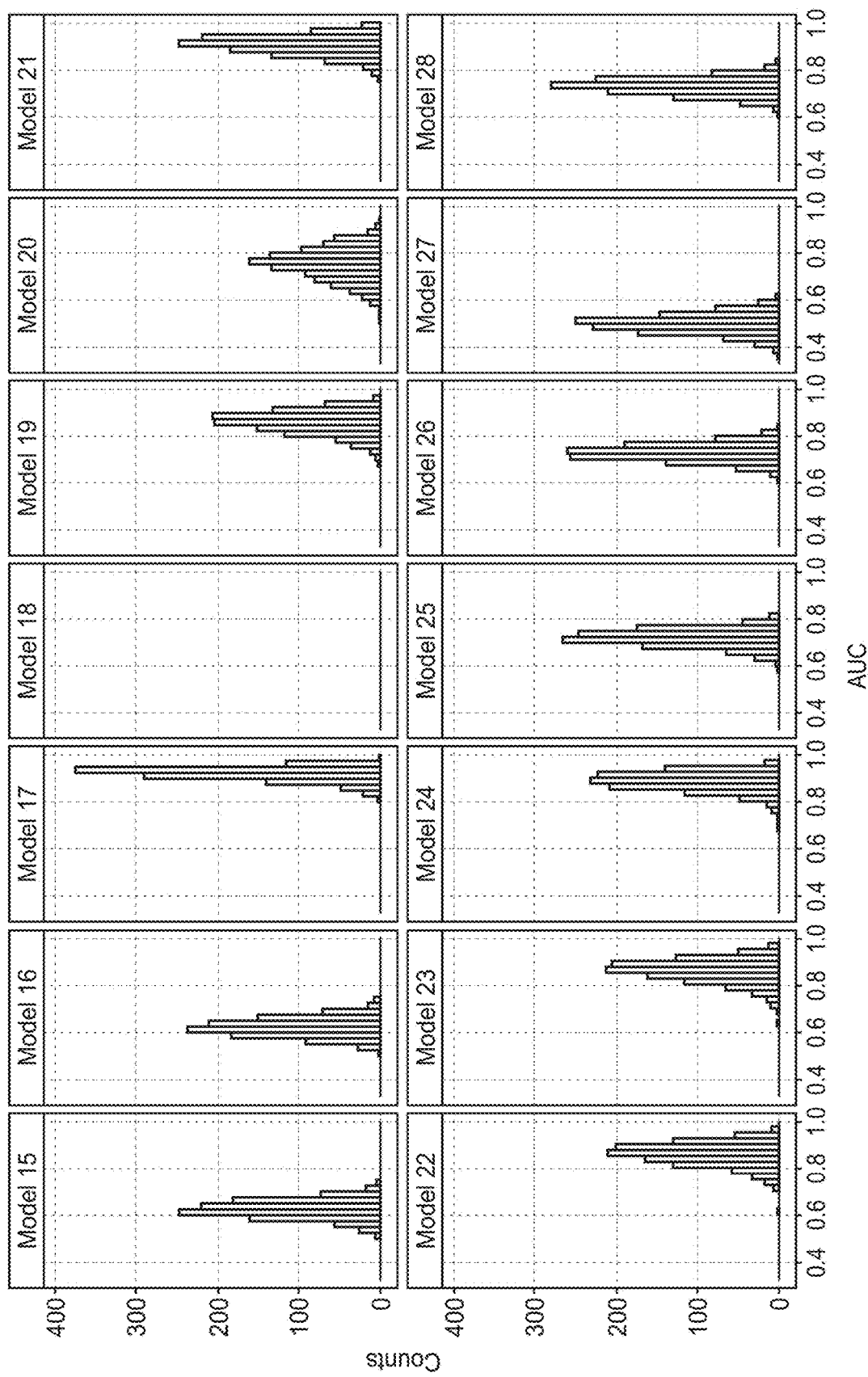
FIG. 6 shows histograms of bootstrapped AUC distributions, according to embodiments of the present disclosure. (Models 2 and 18 did not converge.)
Figure 7:
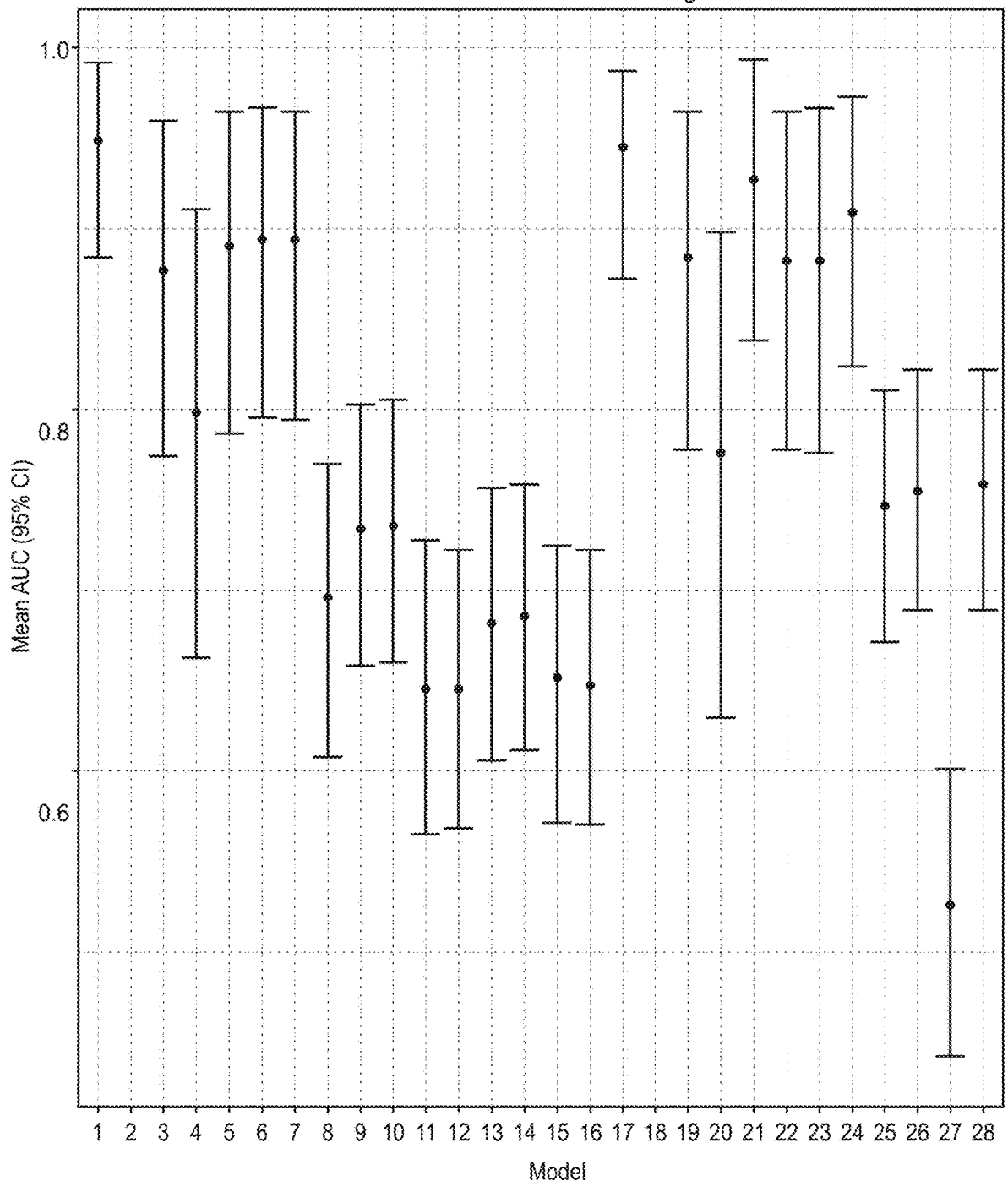
FIG. 7 shows a graph of mean and 95% confidence intervals from bootstrapped AUC distributions, according to embodiments of the present disclosure. (Models 2 and 18 did not converge.)

FIG. 6 shows histograms of bootstrapped AUC distributions for each model. FIG. 7 shows the mean of these AUC distributions along with the upper and lower limits of each distribution's 95% confidence interval.

Table 2 in FIG. 9 shows model coefficients for models 1, 6, 7, and 17.

Notwithstanding the appended clauses, the disclosure set forth herein is also defined by the following clauses:

1. A method of producing a circulating analyte profile of a subject, comprising:

contacting a blood sample from a subject with a panel of probes for specific binding to two or more analytes selected from the group consisting of: tissue inhibitor of metalloproteinase 1 (TIMP1), anti-angiopoietin-like protein 3 antibody (anti-ANGPTL3), epidermal growth factor receptor (EGFR), pro-surfactant protein B (ProSB), anti-14-3-3 protein theta antibody (anti-YWHAQ), and anti-laminin alpha 1 antibody (anti-LAMR1); and detecting the presence or absence of binding of analytes of the two or more analytes to probes of the panel of probes, to produce a circulating analyte profile of the subject.

2. The method according to Clause 1, wherein the blood sample is contacted with a panel of probes for specific binding to three or more analytes selected from the group consisting of: TIMP1, anti-ANGPTL3, EGFR, ProSB, anti-YWHAQ, and anti-LAMR1.

3. The method according to Clause 1, wherein the blood sample is contacted with a panel of probes for specific binding to four or more analytes selected from the group consisting of: TIMP1, anti-ANGPTL3, EGFR, ProSB, anti-YWHAQ, and anti-LAMR1.

4. The method according to Clause 1, wherein the blood sample is contacted with a panel of probes for specific binding to five or more analytes selected from the group consisting of: TIMP1, anti-ANGPTL3, EGFR, ProSB, anti-YWHAQ, and anti-LAMR1.

5. The method according to Clause 1, wherein the blood sample is contacted with a panel of probes for specific binding to TIMP1, anti-ANGPTL3, EGFR, ProSB, anti-YWHAQ, and anti-LAMR1.

6. The method according to any one of Clauses 1 to 5, wherein detecting the presence or absence of binding of analytes of the two or more analytes comprises quantifying detected analytes.

7. The method according to any one of Clauses 1 to 6, wherein the panel of probes comprises probes for binding to one or more additional analytes selected from the group consisting of: HE4, AGR2, CHGA, LRG1, anti-ANXA1, anti-UBQLN1, IL6, IL8, CXCL2, DEFB1, FGF2, CD97, PPBP, PCT, RAGE, S100A4, S100A8/A9, OPN, and any combination thereof, wherein the method further comprises detecting the presence or absence of binding of the one or more additional analytes to probes of the panel of probes to produce the circulating analyte profile of the subject.

8. The method according to Clause 7, wherein the panel of probes includes probes for binding to 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, or each of the additional analytes.

9. The method according to Clause 7 or Clause 8, wherein detecting the presence or absence of binding of the one or more additional analytes comprises quantifying detected one or more additional analytes.

10. The method according to any one of Clauses 1 to 9, wherein the panel of probes comprises probes for binding to circulating tumor cells, wherein the method further comprises detecting the presence or absence of binding of the circulating tumor cells to probes of the panel of probes to produce the circulating analyte profile of the subject.

11. The method according to Clause 10, wherein detecting the presence or absence of binding of the circulating tumor cells comprises quantifying detected circulating tumor cells.

12. The method according to any one of Clauses 1 to 11, wherein the panel of probes comprises probes for binding to tumor DNA, wherein the method further comprises detecting the presence or absence of binding of tumor DNA to probes of the panel of probes to produce the circulating analyte profile of the subject.

13. The method according to Clause 12, wherein detecting the presence or absence of binding of tumor DNA comprises quantifying detected tumor DNA.

14. The method according to any one of Clauses 1 to 13, wherein the panel of probes comprises probes for specifically binding to 50 or fewer analytes.

15. The method according to any one of Clauses 1 to 13, wherein the panel of probes comprises probes for specifically binding to 40 or fewer analytes.

16. The method according to any one of Clauses 1 to 13, wherein the panel of probes comprises probes for specifically binding to 30 or fewer analytes.

17. The method according to any one of Clauses 1 to 13, wherein the panel of probes comprises probes for specifically binding to 25 or fewer analytes.

18. The method according to any one of Clauses 1 to 17, further comprising diagnosing the subject as having cancer based on the circulating analyte profile.

19. The method according to Clause 18, wherein the diagnosing comprises diagnosing the subject as having stage I, stage II, stage III or stage IV cancer.

20. The method according to Clause 19, wherein the diagnosing comprises diagnosing the subject as having stage I or stage II cancer.

21. The method according to Clause 20, wherein the diagnosing comprises diagnosing the subject as having stage I cancer.

22. The method according to any one of Clauses 18 to 21, wherein the diagnosing is further based on a clinical assessment selected from the group consisting of: clinical imaging, age, sex, cancer history, nodule location, nodule size, nodule border, SUV max, smoking status, and any combination thereof.

23. The method according to any one of Clauses 18 to 22, wherein the cancer is lung cancer.

24. The method according to Clause 23, wherein the lung cancer is non-small cell lung cancer (NSCLC).

25. The method according to any one of Clauses 1 to 24, wherein the subject is from a population having a high risk of lung cancer.

26. The method according to Clause 25, wherein the population having a high risk of lung cancer consists of subjects who currently smoke.

27. The method according to Clause 25 or Clause 26, wherein the population having a high risk of lung cancer consists of past heavy smokers.

28. The method according to any one of Clauses 1 to 27, wherein the subject has an indeterminate lung lesion.

29. The method according to any one of Clauses 1 to 24, wherein the subject is undergoing lung cancer therapy, and wherein the method further comprises predicting, monitoring, or both, the therapeutic response of the subject to the lung cancer therapy based on the circulating analyte profile.

30. The method according to any one of Clauses 1 to 29, wherein the blood sample is a whole blood sample, a plasma sample, or a serum sample.

31. The method according to any one of Clauses 1 to 30, wherein the panel of probes is a panel of capture probes provided as an addressable probe array.

32. The method according to Clause 31, wherein the addressable probe array is present on a magnetic sensor chip of a magnetic sensor device.

33. The method according to Clause 32, wherein the magnetic sensor chip comprises two or more magnetic sensors having capture probes attached to the surface thereof.

34. The method according to Clause 33, wherein each of the two or more magnetic sensors having capture probes attached to the surface thereof comprises capture probes for binding to the same two or more analytes.

35. The method according to Clause 33 or Clause 34, wherein each magnetic sensor comprises a magnetoresistive element.

36. The method according to Clause 35, wherein the magnetoresistive element is a spin valve magnetoresistive element or a magnetic tunnel junction (MTJ) magnetoresistive element.

37. The method according to any one of Clauses 32 to 36, wherein detecting the presence of binding of the two or more analytes to probes of the panel of probes comprises detecting a magnetically-labeled detection reagent bound to a captured analyte.

38. The method according to Clause 37, wherein the magnetically-labeled detection reagent is bound indirectly to the captured analyte.

39. The method according to Clause 38, wherein the magnetically-labeled detection reagent is part of a complex comprising the capture probe, the analyte, a primary detection reagent specifically bound to the analyte, and the magnetically-labeled detection reagent bound to the primary detection reagent.

40. The method according to any one of Clauses 35 to 39, wherein detecting the presence of binding of the two or more analytes to probes of the panel of probes comprises detecting a resistance change in the magnetoresistive element induced by the magnetically-labeled detection reagent.

41. A sensor device, comprising:
  a panel of capture probes provided as an addressable probe array, wherein the panel comprises probes for specific binding to two or more analytes selected from the group consisting of: TIMP1, anti-ANGPTL3, EGFR, ProSB, anti-YWHAQ, and anti-LAMR1.

42. The sensor device of Clause 41, wherein the panel comprises probes for specific binding to three or more analytes selected from the group consisting of: TIMP1, anti-ANGPTL3, EGFR, ProSB, anti-YWHAQ, and anti-LAMR1.

43. The sensor device of Clause 41, wherein the panel comprises probes for specific binding to four or more analytes selected from the group consisting of: TIMP1, anti-ANGPTL3, EGFR, ProSB, anti-YWHAQ, and anti-LAMR1.

44. The sensor device of Clause 41, wherein the panel comprises probes for specific binding to five analytes selected from the group consisting of: TIMP1, anti-ANGPTL3, EGFR, ProSB, anti-YWHAQ, and anti-LAMR1.

45. The sensor device of Clause 41, wherein the panel comprises probes for specific binding to TIMP1, anti-ANGPTL3, EGFR, ProSB, anti-YWHAQ, and anti-LAMR1.

46. The sensor device of any one of Clauses 41 to 45, wherein the panel of probes comprises probes for binding to one or more additional analytes selected from the group consisting of: HE4, AGR2, CHGA, LRG1, anti-ANXA1, anti-UBQLN1, IL6, IL8, CXCL2, DEFB1, FGF2, CD97, PPBP, PCT, RAGE, S100A4, S100A8/A9, OPN, and any combination thereof.

47. The sensor device of any one of Clauses 41 to 45, wherein the panel of probes comprises probes for binding to 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, or each of the additional analytes.

48. The sensor device of any one of Clauses 41 to 47, wherein the panel of probes comprises probes for binding to circulating tumor cells.

49. The sensor device of any one of Clauses 41 to 48, wherein the panel of probes comprises probes for binding to tumor DNA.

50. The sensor device of any one of Clauses 41 to 49, wherein the panel of probes comprises probes for binding to 50 or fewer analytes.

51. The sensor device of any one of Clauses 41 to 49, wherein the panel of probes comprises probes for binding to 40 or fewer analytes.

52. The sensor device of any one of Clauses 41 to 49, wherein the panel of probes comprises probes for binding to 30 or fewer analytes.

53. The sensor device of any one of Clauses 41 to 49, wherein the panel of probes comprises probes for binding to 25 or fewer analytes.

54. The sensor device of any one of Clauses 41 to 53, wherein the sensor device is a magnetic sensor device.

55. The sensor device of Clause 54, wherein the magnetic sensor device comprises a magnetic sensor chip comprising the panel of capture probes.

56. The sensor device of Clause 55, wherein the magnetic sensor chip comprises two or more magnetic sensors having capture probes attached to the surface thereof.

57. The sensor device of Clause 56, wherein each of the two or more magnetic sensors having capture probes attached to the surface thereof comprises capture probes for binding to the same analyte.

58. The sensor device of Clause 56 or 57, wherein each magnetic sensor comprises a magnetoresistive element.

59. The sensor device of Clause 58, wherein the magnetoresistive element is a spin valve magnetoresistive element or a magnetic tunnel junction (MTJ) magnetoresistive element.

Although the foregoing embodiments has been described in some detail by way of illustration and example for purposes of clarity of understanding, it is readily apparent to those of ordinary skill in the art in light of the teachings of this present disclosure that certain changes and modifications may be made thereto without departing from the spirit or scope of the appended claims.

Accordingly, the preceding merely illustrates the principles of embodiments of the present disclosure. It will be appreciated that those skilled in the art will be able to devise various arrangements which, although not explicitly described or shown herein, embody the principles of the subject embodiments and are included within its spirit and scope. Furthermore, all examples and conditional language recited herein are principally intended to aid the reader in understanding the principles of embodiments of the present disclosure and the concepts contributed by the inventors to furthering the art, and are to be construed as being without limitation to such specifically recited examples and conditions. Moreover, all statements herein reciting principles, aspects, and embodiments of the present disclosure as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present disclosure, therefore, is not intended to be limited to the exemplary embodiments shown and described herein. Rather, the scope and spirit of present disclosure is embodied by the appended claims.

That which is claimed is:

1. A sensor device, comprising:
 a panel of capture probes provided as an addressable probe array, wherein the panel comprises capture probes for specific binding to analytes comprising: tissue inhibitor of metalloproteinase 1 (TIMP1), anti-angiopoietin-like protein 3 antibody (anti-ANGPTL3), epidermal growth factor receptor (EGFR), pro-surfactant protein B (ProSB), anti-14-3-3 protein theta antibody (anti-YWHAQ), and anti-laminin alpha 1 antibody (anti-LAMR1).

2. The sensor device of claim 1, wherein the panel of capture probes comprises probes for binding to one or more additional analytes selected from the group consisting of: human epididymis protein 4 (HE4), anterior gradient protein 2 (AGR2), chromogranin A (CHGA), leucine-rich alpha-2-glycoprotein 1 (LRG1), anti-annexin 1 antibody (anti-ANXA1), anti-ubiquilin 1 antibody (anti-UBQLN1), interleukin 6 (IL6), interleukin 8 (IL8), chemokine (C-X-C motif) ligand 2 (CXCL2), defensin, beta 1 (DEFB1), fibroblast growth factor 2 (FGF2), cluster of differentiation 97 (CD97), pro-platelet basic protein (PPBP1), procalcitonin (PCT), receptor for advanced glycation endproducts (RAGE), S100 calcium-binding protein A4 (S100A4), S100 calcium-binding protein A8/A9 complex (S100A8/A9), osteopontin (OPN), and any combination thereof.

3. The sensor device of claim 1, wherein the panel of capture probes comprises probes for binding to circulating tumor cells, tumor DNA, or both.

4. The sensor device of claim 1, wherein the panel of capture probes comprises probes for binding to tumor DNA.

5. The sensor device of claim 1, wherein the panel of capture probes comprises probes for binding to 50 or fewer analytes.

6. The sensor device of claim 1, wherein the sensor device is a magnetic sensor device.

7. The sensor device of claim 6, wherein the magnetic sensor device comprises a magnetic sensor chip comprising the panel of capture probes.

* * * * *